United States Patent [19]
Briles et al.

[11] Patent Number: 6,027,734
[45] Date of Patent: *Feb. 22, 2000

[54] MUCOSAL ADMINISTRATION OF PNEUMOCOCCAL ANTIGENS

[75] Inventors: David E. Briles; Hong-Yin Wu, both of Birmingham, Ala.

[73] Assignee: UAB Research Foundation, Birmingham, Ala.

[*] Notice: This patent is subject to a terminal disclaimer.

[21] Appl. No.: 08/312,949

[22] Filed: Sep. 30, 1994

Related U.S. Application Data

[63] Continuation-in-part of application No. 08/246,636, May 20, 1994, which is a continuation-in-part of application No. 08/048,896, Apr. 20, 1993, which is a continuation-in-part of application No. 07/835,698, Feb. 12, 1992, which is a continuation-in-part of application No. 07/656,773, Feb. 15, 1991, abandoned.

[51] Int. Cl.$^7$ .......................... A61K 39/09; A61K 39/00; A01N 63/00
[52] U.S. Cl. ...................... 424/244.1; 424/93.44; 424/184.1; 424/282; 424/282.1; 424/289; 424/289.1
[58] Field of Search ............... 424/244.1, 184.1, 424/282.1, 93.44, 289.1, 289, 184, 282

[56] References Cited

U.S. PATENT DOCUMENTS

| | | | |
|---|---|---|---|
| 4,873,890 | 10/1989 | Clancey et al. | 424/451 |
| 5,182,109 | 1/1993 | Tamura et al. | 424/92 |

FOREIGN PATENT DOCUMENTS

| | | | |
|---|---|---|---|
| 303804 | 5/1991 | WIPO | A61K 39/11 |
| 9214488 | 8/1992 | WIPO . | |

OTHER PUBLICATIONS

Anonymous. Centers for Disease Control HIV/AIDS Serveillance Report. 1991; Aug. :1–18.

Fraser DW. What are our bacterial disease problems. In: JB Robbins, Hill JC, Sadoff JC ed. Bacterial Vaccines. New York: 1982: xix–xxiv.

Berman S. McIntosh K. Selective primary health care: stratagies for control of disease in the developing world. XXI acute respiratory infections. Rev. Infect. Dis. 1985; 7 :647–491.

Greenwood BM, Greenwood AM, Bradley AK, Tulloch S, Hayes R, Oldfield FSJ. Deaths in infancy and early childhood in a well vaccinated, rural, West African population. Ann. Trop. Pediatr. 1987; 7 :91–99.

Spika JS, Munshi MH, Wojtyaniak B, Sack DA, Hossain A, Rahman M, Saha SK. Acute lower respiratory infections: a major cause of death in children in Bangladesh. Ann. Trop. Pediatr. 1989; 9 :33–39.

Bale Jr. Etiology and epidemiology of acute respiratory tract infections in children in developing countries. Rev. Infect. Dis. 1990; 12 (Suppl 8) :S861–S1083.

Munoz R, Musser JM, Crain M, Briles DE, Marlon A, Parkinson AJ, Sorensen U, Tomasz A. Geographic distribution of penicillin–resistant clones of *Streptococcus pneumoniae:* characterization by penicillin–binding protein profile, surface protein A typing, and multilocus enzyme analysis. Clinic. Infect. Dis. 1992; 15 :112–118.

Marton A, Gulyas M, Munoz R, Tomasz A. Extremely high incidence of antibiotic resistance in clinical isolates of *Streptococcus pneumoniae* in Hungary. J. Infect. Dis. 1991; 163 :542–548.

Klugman KP. Pneumococcal resistance to antibiotics. Clin. Microbiol. Rev. 1990.

Gray BM, Converse GM III, Dillon HC. Epidemiologic studies of *Streptococcus pneumoniae* in infants: acqusition, carriage, and infection during the first 24 months of life. J. Infect. Dis. 1980; 142 :923–933.

Gray BM, Converse GM III, Huhta N, Johnston RB Jr., Pichichero ME, Schiffman G, Dillon HC Jr. Antibody response to pneumococcal carriage. J. Infect. Dis. 1981; 142 : 312–318.

Hendley JO, Sande MA, Stewart PM, et al, Spread of *Stereptococcus pneumoniae* in families. I. Carriage rates and distribution of types. J. Infect. Dis. 1975; 132 :55.

Smillie WG, Warnock GH, White HJ. A study of a type I pneumococcus epidemic at state hospital at Worchester Massachusettes. Am J Pub Hlth 1938; 28 :293–302.

Smillie WG. A study of an outbreak of type II pneumococcal pneumonia in the Veterans Administration Hospital at Bedford, Massachusetts. Am. J. Hyg. 1936; 24 :522–535.

Gratten M, Naraqi S, Hansman D. High prevalence of penicillin–insensitive penumococci in port moresby, Paupa New Guinea. Lancet 1980; ii :192–195.

DeMaria TF, McGhee RB, Lim DJ. Rheumatoid factor in otitis media with effusion. Arch. Otolaryngol. 1984; 110:279–280.

Bohr V, Rasmussen N, Hansen B, Gade A, Kjersem H, Johsen N, Paulson O. Pheumococcal meningitis: An evaluation of prognostic factors in 164 cases based on mortality and on a study of lasting sequelae. J. Infect. Dis. 1985; 10:143–157.

Klein JO. The epidemiology of pneumococcal diseases in infants and children. Rev. Infect. Dis. 1981; 3 :246.

(List continued on next page.)

*Primary Examiner*—James C. Housel
*Assistant Examiner*—Rodney P. Swartz
*Attorney, Agent, or Firm*—Frommer Lawrence & Haug LLP; William S. Frommer; Thomas J. Kowalski

[57] ABSTRACT

Mucosal administration, particularly intranasally, of killed whole pneumococci, lysate of pneumococci and isolated and purified PspA, as well as immunogenic fragments thereof, particularly when administered with cholera toxin B subunit, provides protection in animals against pneumococcal colonization and systemic infection. The ability to elicit protection against pneumococcal colonization in a host prevents carriage among immunized individuals, which can lead to elimination of disease from the population as a whole.

9 Claims, 8 Drawing Sheets

OTHER PUBLICATIONS

Bolan G, Broome CV, Facklam RR, Plikaytis BD, Fraser WD, Schlech WFI. Pneumococcal vaccine efficacy in selected populations in the United States. Ann. Intern. Med. 1986; 104 :1–6.

Shapiro ED, Berg AT, Austrian R, Schroeder D, Parcells V, Margolis A, Adair RK, Clemmens JD. Protective efficacy of polyvalent pneumococcal polysaccharide vaccine. N. Engl. J. Med 1991; 325 :1453–1460.

Cowan MJ, Ammann AJ, Wara DW, Howie VM, Schultz L, Doyle N, Kaplan M. Pneumococcal polysaccharide immunization in infants and children. Pediatrics 1978; 62:721–727.

Gotschlich EC, Goldschneider I, Lepow ML, Gold R. The immune response to bacterial polysaccharides in man. Antibodies in human diagnosis and therapy.. New York: Raven, 1977: 391–402.

Barbour ML, Mayon–White RT, Crook DW, Coles C, Moxon ER. The influece of Haemophilus influenzae type b (HIB) conjugate vaccine (PRP–T) on oropharyngeal carriage of Hib in infants under 12 months of age. ICAAC Abstracts 1993; 33 :175.

Chiu SS, Greenberg PD, Marcy SM, Wong VK, Chang SJ, Chiu CY, Ward JI. Mucosal antibody responses in infants following immunization with Haemophilus influenzae. Pediatric Res. Abstracts 1994; 35 :10A.

Fallon MT, Reinhard MK, Gray BM, Davis TW, Lindsey JR, Inapparent Streptococcus pneumoniae type 35 infections in commercial rats and mice. Laboratory Animal Science 1988; 38 :129.

Douglas RM, D H, Miles HB, Paton JC. Pneumococcal carriage and type–specific antibody Failure of a 14–valent vaccine to reduce carriage in healthy children. American Journal of Diseases of Children 1986; 140 :1183–1185.

Douglas RM, Miles HB. Vaccination against Streptococcus pneumoniae in childhood: lack of demonstrable benefit in young Australian children. Journal of Infectious Diseases 1984; 149 :861–869.

Mestecky J. The common mucosal immune system and current strategies for induction of immune response in external secretions. J. Clin. Immunol. 1987; 7 :265–276.

Croitoru K, Bienenstock J. Characteristics and functions of mucosa–associated lymphoid tissue. In: PL Ogra, Mestecky J, Lamm ME, Strober W, McGhee JR, Bienenstock J ed. Handbook of Mucosal Immunology. San Diego, CA: Academic Press, Inc., 1994: 141–149.

Bienenstock J, Johnston N, Perey DY. Bronchial lymphoid tissue. I. Morphologic characteristics. Lab. Invest. 1973; 28 :686–692.

Bienenstock J, Johnston N, Perey DY. Bronchial lymphoid tissue. II. Functional characteristics. Lab. Invest. 1973; 28 : 693–698.

Pabst R. Is BALT a major component of the human lung immune system? Immunology Today 1992; 13 :119–122.

Kuper CF, Koornstra PJ, Hameleers DMH, Biewenga J, Spit BJ, Duijvestijn AM, van Breda Vriesman PJC, Sminia T. The role of nasopharyngeal lymphoid tissue. Immunol. Today 1992; 13 :219–224.

Wu H–Y, Russell MW. Induction of mucosal immunity by intranasal application of a streptococcal surface protein antigen with the cholera toxin B subunit. Infection and Immunity 1993; 61 :314–322.

Russell MW, Wu H–Y. Distribution, persistence, and recall of serum and salivary antibody responses to peroral immunization with protein antigen I/II of Streptococcus mutants coupled to the cholera toxin B sununit. Infection and Immunity 1991; 59 :4061–4070.

Elson, CO, Ealding W. Generalized systemic and mucosal immunity in mice after mucosal stimulation with cholera toxin. J. Immunol. 1984; 132 :2736–2741.

Elson CO. Cholera toxin and its subunits as potential oral adjuvants. Curr. Topics Microbiol. Immunol. 1989; 146:29–33.

Lycke N, Holmgren J. Strong adjuvant properties of cholera toxin on gut mucosal immune responses to orally presented antigens. Immunology 1986; 59 :301–308.

Wilson AD, Stokes CR, Bourne FJ. Adjuvant effect of cholera toxin on the mucosal immune response to soluble proteins. Differences between mouse strains and protein antigens. Scand. J. Immunol. 1989; 29 :739–745.

Wilson AD, Clarke CJ, Stokes CR. Whole cholera toxin and B subunit act synergistically as an adjuvant for the mucosal immune response of mice to keyhole limpet haemocyanin. Scand. J. Immunol. 1990; 31 :443–451.

Czerkinsky C, Russell MW, Lycke N, Lindblad M, Holmgren J. Oral administration of a streptococcal antigen coupled to cholera toxin B subunit evokes strong antibody responses in salivary glands and extramucosal tissues. Infect. Immun. 1989; 57 :1072–1077.

Holmgren J, Lycke N, Czerkinsky C. Cholera toxin and cholera B subunit as oral–mucosal adjuvant and antigen vector systems. Vaccine 1993; 11 :1179–1184.

Quiding M, Nordström I, Kilander A, Anderson G. Hanson LÅ, Holmgren J, Czerkinsky C. Intestinal immune responses in humans. Oral cholera vaccination induces strong intestinal antibody responses and interferon–λ production and evokes local immunological memory. J. Clin. Invest. 1991; 88 :143–148.

Svennerholm AM, Jertborn M, Gothefors L, Karim AMMM, Sack DA, Holmgren J. Mucosal antitoxin and antibacterial immunity after cholera disease and after immunization with a combined B subunit–whole cell vaccine. J. Infect. Dis. 1984; 149 :884–893.

Lycke N, Tsuji T, Holmgren J. The adjuvant effect of Vibrio cholerae and E. coli heat labile enterotoxins is linked to the ability to stimulate cAMP. European Journal of Immunology 1992; 22 :2277–2281.

Lycke N, Karlsson U, Sjölander A, Magnusson K–E. The adjuvant action of cholera toxin is associated with an increased intestinal permeability for luminal antigens. Scandinavian Journal of Immunology 1991; 33 :691–698.

Gizurarson S, Tamura S, Kurata T, Hasiguchi K, Ogawa H. The effect of cholera toxin and cholera toxin B subunit on the nasal mucosa membrane. Vaccine 1991; 9 :825–832.

Bromander A, Holmgren J, Lycke N. Cholera toxin stimulates IL–1 production and enhances antigen presentation by macrophages in vitro. Journal of Immunology 1991; 146 : 2908–2914.

Anastassiou ED, Yamada H, Francis ML, Mond JJ, Tsokos GC. Effects of Cholera toxin on human B cells. Cholera toxin induces B cell surface DR expression while it inhibits anti–$\mu$ antibody–induced cell proliferation. J. Immunol. 1990; 145 :2375–2380.

Muñoz E, Zubiaga AM, Merrow M, Sauter NP, Huber BT. Cholera toxin discriminates between T helper 1 and 2 cells in T cell receptor–mediated activation: Role of cAMP in T cell proliferation. J. Exp. Med. 1990; 172 :95–103.

Lycke N, Strober W. Cholera toxin promotes B cell isotype differentiation. J. Immunol. 1989; 142 :3781–3787.

Wilson AD, Bailey M, Williams NA, Stokes CR. The in vitro production of cytokines by mucosal lymphocytes immunized by oral administration of keyhole limpet hemocyanin using cholera toxin as an adjuvant. European Journal of Immunology 1991; 21 :2333–2339.

Briles DE, Claflin JL, Schroer K, Forman C. Mouse IgG3 antibodies are highly protective against infection with *Streptococcus pneumoniae*. Nature 1981; 294 :88–90.

Lock RA, Paton JC, Hansman D. Comparative efficacy of pneumococcal neuraminidase and pneumolysin as immunogens protective against *Streptococcus pneumoniae*. Microb. Pathog. 1988; 5 :461–467.

Lock RA, Hansman D, Paton JC. Comparative efficacy of autolysin and pneumolysin as immunogens protecting mice against infection by *Streptococcus pneumoniae*. Microbial Pathogenesis 1992; 12 :137–143.

Converse GM III, Dillon HC Jr. Epidemiological studies of *Streptococcus pneumoniae* in infants: methods of isolating pneumococci. J. Clin. Micro. 1977; 5 :293–296.

Francis ML, Ryan J, Jobling MG, Holmes RK, Moss J, Mond JJ. Cyclic AMP–independent effects of cholera toxin on B cell activation. II. Binding of ganglioside $G_{M1}$ induces B cell activation. Journal of Immunology 1992; 148:1999–2005.

Woogen SD, Ealding W, Elson CO. Inhibition of murine lymphocyte proliferation by the B subunit of cholera toxin. Journal of Immunology 1987; 139 :3764–3770.

Garrone P, Banchereau J. Agonistic and antagonistic effects of cholera toxin on human B lymphocyte proliferation. Molecular Immunology 1993; 30 :627–635.

Haack BM, Emmrich F, Resch K. Cholera toxin inhibits T cell receptor signaling by covalent modification of the CD3–ζ subunit. Journal of Immunology 1993; 150:2599–2606.

Abraham E, Robinson A. Oral Immunization with bacterial polysaccharide and adjuvant enhances antigen–specific pulmonary secretory antibody response and resistance to pneumonia. Vaccine 1991; 9 :757–764.

Szu SC, Li X, Schneerson R, Vickers JH, Bryla D, Robbins JB. Comparative immunogenicities of Vi polysaccharide–protein conjugates composed of cholera toxin or its B subunit as a carrier bound to high– or lower–molecular–weight Vi. Infect. Immun. 1989; 57 :3823–3827.

Chen K–S, Strober W. Cholera holotoxin and its B subunit enhance Peyer's patch B cell responses induced by orally administered influenza virus: disproportionate cholera toxin enhancement of the IgA B cell response. Eur. J. Immunol. 1990; 20 :433–436.

Liang X, Lamm ME, Nedrud JG. Oral administration of cholera toxin–Sendai virus conjugate potentiates gut and respiratory immunity against Sendai virus. Journal of Immunology 1988; 141 :1495–1501.

Brimblecombe FSW, Cruicshank R, Masters PL, Reid DD, Stewart GT. Family studies of respiratory infections. British Medical Journal 1958; :119–128.

Masters PL, Brumfitt W, Mendez RL, Likar M. Bacterial flora of the upper respiratory tract in Paddington families, 1952–1954, Brit. Med. J. 1958; 1 :1200–1205.

Gwaltney JM, Sande MA, Austrian R, al. e. Spread of *streptococcus pneumoniae* in families: II Relation of transfer of *Streptococcus pneumoniae* to incidence of colds and serum antibody. J. Infect. Dis. 1975; 132 :62.

Russell MW, Prince SJ, Ligthart GJ, Mestecky J, Radl J. Comparison of salivary and serum antibodies to common environmental antigens in elderly, edentulous, and normal adult subjects. Aging Immunol. Infect. Dis. 1990; 2:275–286.

Bessen D, Fischetti VA. Influence of intranasal immuniation with synthetic peptides corresponding to conserved epitopes of M protein on mucosal immunization by group A streptococci. Infect. Immun. 1988; 56 :2666–2672.

Hollingshead SK, Simecka JW, Michalek SM. Role of M protein in pharyngeal colonization by group A streptococci in rats. Infect. Immun. 1993; 61 :2277–2283.

Kauppi M, Eskola J, Kathty H. H. influenzae type b (Hib) conjugate vaccines induce mucosal IgA1 and IgA2 antibody responses in infants and children. ICAAC Abstracts 1993; 33 :174.

Briles DE, Forman C, Horowitz JC, Volanakis JE, Benjamin WH Jr., McDaniel LS, Eldridge J, Brooks J. Antipneumococcal effects of C–reactive protein and monoclonal antibodies to pneumococcal cell wall and capsular antigens. Infect. Immun. 1989; 57 :1457–1464.

Bixler et al Synthetic Vaccines. vol. 1 pp. 39–71 1987.

van de Wijgert et al, Infection & Immunity, 59:2750–57, 1991.

Fontanges et al Rev. Fr. Allergol 17:35–41, 1977 Abstract only.

Garcia et al FEMS Microbiol Lett. 108:163–167, 1993, Abstract only.

Germie et al (Novel Vaccine Strategies : Mucosal Immunization, Adjuvants & Genetic Approaches Oct. 1993, Abstract only.

Bessen et al Journ of Immunology 1990 vol. 145: 1251–1256.

Wu et al Infection & Immunity 61:314–322 1993.

Gupta et al Vaccines 13:1263–1276, 1995.

Kurl et al ACTA Path Microbiol Immunol 93:401–405, 1985 Abstract only.

McDaniel et al, Infect & Immunity 59:222–228 1991.

Talkington et al Infection & Immunity 59:1285–1289, 1991.

```
                        a   b   c   d   e   f   g
GLU GLU ser pro val ala ser gln ser LYS ala GLU LYS ASP  14
                            tyr ASP ala ala LYS LYS ASP  21
                            ala LYS asn ala LYS LYS ala  28
                            val GLU ASP ala gln LYS ala  35
                            leu ASP ASP ala LYS ala ala  42
                            gln LYS LYS                  45
```

| | | | | | | | | | | |
|---|---|---|---|---|---|---|---|---|---|---|
| 1381 / TCA ser | | | | | | | 1411 GGT gly | TCA ser | 471 TGG trp | TAC tyr | TAC tyr | CTC leu | AAC asn | AGC ser | AAT asn | GGT gly |
| 1441 / ATG met | 461 GCG ala | ACA thr | GGA gly | TGG trp | CTC leu | CAA gln | AAC asn | 1471 GGT gly | TCA ser | 491 TGG trp | TAC tyr | TAC tyr | CTC leu | AAC asn | AGC ser | AAC asn | GGC gly |
| 1501 / GCT ala | 481 GCT ala | ACA thr | GGT gly | TGG trp | CTC leu | CAA gln | AAT asn | 1531 GGT gly | TCA ser | 511 TGG trp | TAT tyr | TAC tyr | CTC leu | AAC asn | GCT ala | AAC asn | GGT gly |
| 1561 / GCT ala | 501 GCA ala | ACA thr | GGT gly | TGG trp | GCT ala | AAA lys | TAC tyr | 1591 GGT gly | TCA ser | 531 TGG trp | TAC tyr | TAC tyr | CTC leu | AAC asn | GCT ala | AAT asn | GGC gly |
| 1621 / GCT ala | 521 GCT ala | ACA thr | GGT gly | TGG trp | CTC leu | CAA gln | TAC tyr | 1651 GGT gly | TCA ser | 551 TGG trp | TAC tyr | TAC tyr | CTC leu | AAC asn | GCT ala | AAC asn | GGT gly |
| 1681 / GCT ala | 541 GCA ala | ACA thr | GGT gly | TGG trp | GCT ala | AAA lys | GTC val | 1711 GGT gly | TCA ser | 571 TGG trp | TAC tyr | TAC tyr | CTC leu | AAC asn | GCT ala | AAT asn | GGT gly |
| 1741 / GCT ala | 561 GCT ala | ACA thr | GGT gly | TGG trp | CTC leu | CAA gln | TAC tyr | 1771 GGT gly | TCA ser | 591 TGG trp | TAC tyr | TAC tyr | CTC leu | AAC asn | GCT ala | AAC asn | GGC gly |
| 1801 / GCT ala | 581 GCT ala | ACA thr | GGT gly | TGG trp | CTC leu | CAA gln | GTC val | 1831 GGT gly | TCA ser | 611 TGG trp | TAC tyr | TAC tyr | CTC leu | AAC asn | GCT ala | AAT asn | GGT gly |
| 1861 / GCT ala | 601 GCA ala | GCA ala | AGC ser | CAA gln | GTG val | GAT asp | GGA gly | 1891 GAT asp | ACC ser | 631 TGG trp | TGG trp | TAT tyr | CTT leu | GAA glu | GCA ala | TCA ser | TTA leu |
| 1921 / GCT ala | 621 AAA lys | GCA ala | GTC val | AAC asn | TGG trp | TTC phe | GTA val | 1951 TCA ser | GAT asp | 651 AAA lys | GTC val | TAT tyr | GCC ala | GTC val | AAT asn | GGT gly | TGG trp |
| 1981 / GCC ala | 641 CTT leu | GAT asp | TAA OCH | ATT ile | ACA thr | ACT thr | TGT cys | GGC gly | TAT tyr | 671 AAA lys | ACA thr | AAT asn | TAA OCH | AAT asn | AAT asn | GAA glu | AAA lys |
| 2041 / TAA OCH | 661 GCC ala | GAT asp | TTG leu | AAT asn | AAA lys | AAA lys | ATG met | GAA glu | CAT his | TTG leu | TTT phe | TTT phe | | | | | |
| 2041 / AAG lys | 681 CTT leu | CGA arg | | AGA arg | | | | GTA val | | 691 TTT phe | TAC tyr | | TAA OCH | | TGA OPA | | |

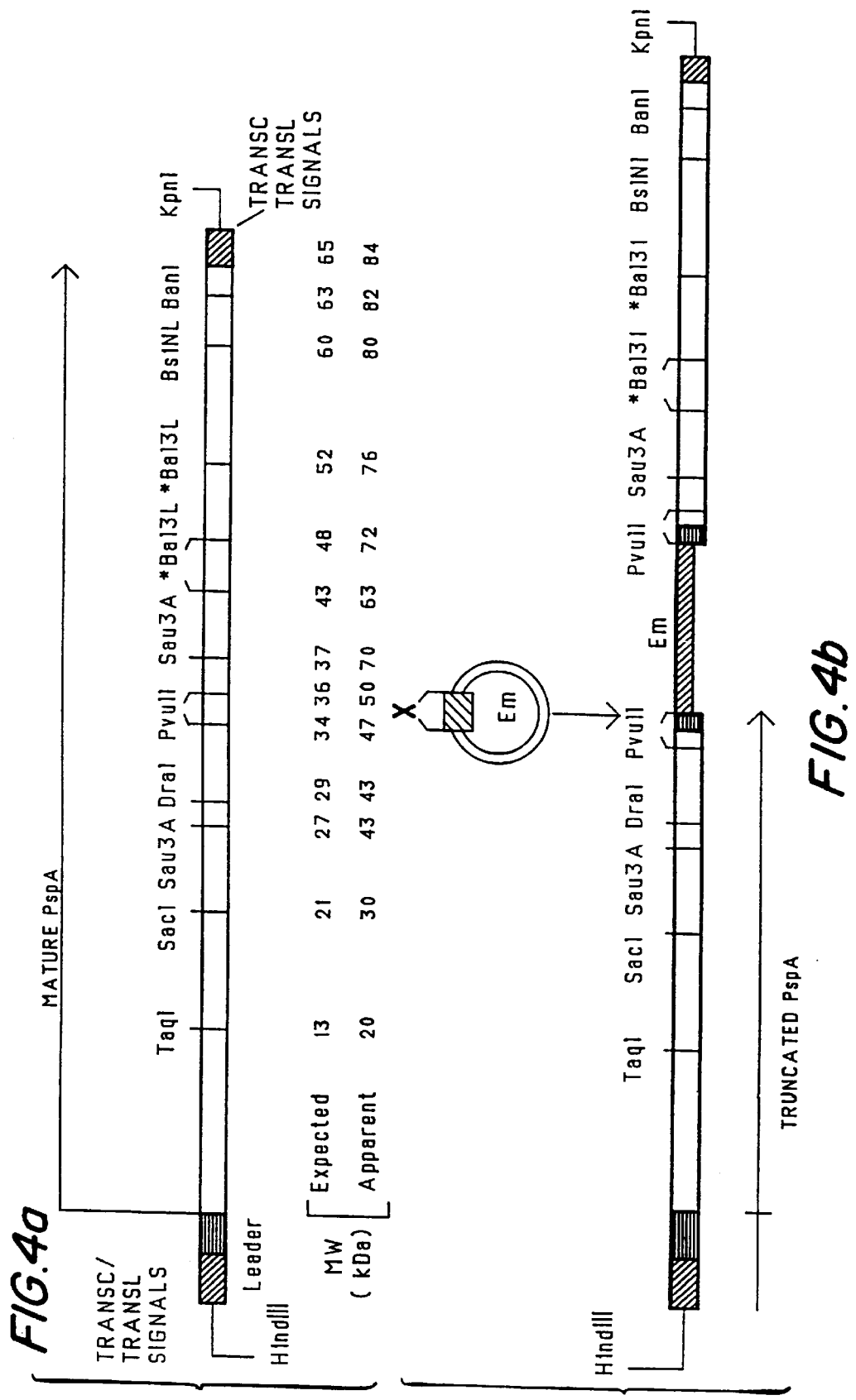

Location of epitopes detected by monoclonal antibodies to PspA

|  |  | a | b | c | d | e | f | g |
|---|---|---|---|---|---|---|---|---|
|  | 1 | E | E | s | p | y | a | s |
|  | 8 | Q | s |  |  |  |  |  |
|  | 15 | y | D | K | a | E | K | D |
|  | 22 | a | K | a | a | K | K | D |
|  | 29 | y | E | N | a | K | K | a |
|  | 36 | L | D | D | a | Q | K | a |
| XI1526* | 43 | Q | K | D | a | K | a | a |
| XI126* | 50 | Q | K | K | y | D | E | D |
| XIR35 | 57 | a | a | K | t | E | E | K |
| XIR148 | 64 | s | E | L | E | K | a | a |
| XIR1224 | 71 | y | a | E | m | D | K | a |
|  | 78 | y | L | a | y | Q | Q | a |
|  | 85 | t | D | a | y | Q | Q | a |
|  | 92 | a |  | K | a | a | K | D |
|  | 97 | L | D | E | a | D | K | m |
|  | 104 | E | E | E | a | K | K | R |
|  | 111 | L | N | t | y | R | t | K |
|  | 118 | y | y | p | E | p | a | m |
|  | 125 | L | a | E | t | K | E | Q |
| 138 HHHHH | 132 | s | E | E | a | K | K | K |
|  | 139 | a | p | E | L | t | Q | K |
|  | 146 | L | E | E | a | K | K | K |
|  | 153 | L | E | E | a | E | a | K |
|  | 160 | a | t | E | a | K | K | K |
| XIR16 | 167 | y | D |  |  |  | Q | K |
|  | 174 | p | Q | a | a | E | E | a |
|  |  |  |  |  |  |  | y |  |
|  | 178 | L | a | E | L | E | N | K |
|  | 185 | y | H | R | L | E | Q | Q |
| 193 HHHHH | 192 | L | K | E | L | D | E | E |
|  | 199 | E |  |  |  |  |  | s |
|  | 204 | a | K | E | s | E | D | y |
|  | 211 | p | L | Q | g | L | R | a |
|  | 218 | a | K | K | s | K | L | D |
| XI64* | 225 | K |  |  | a |  |  | s |
| XIR278* |  |  |  |  |  |  |  |  |
| XI1325* | 226 | L | E | E | L | s | D | K |
|  | 233 | L | D | E | L | D | a | E |
|  | 240 | L | a | K | L | E | D | Q |
|  | 247 | L | K | a | a | E | E | N |
|  | 254 |  | N | N | y | E | D | y |
| 261 HHHHH | 260 | L | K | E | g | L | E | K |
|  | 267 | t | L | a | a | K | K | a |
| XI1323* | 274 | E |  |  |  |  |  |  |
|  | 275 | L | E | K | t | E | a | D |
|  | 282 | L | K | K | a | y | N | E |

ANTIBODY REACTIVITY

| | Xi 126 | XiR 1224 | XiR 148 | XiR 1526 | XiR 35 | XiR 16 | XiR 278 | XiR 1325 | XiR 64 | XiR 1323 |
|---|---|---|---|---|---|---|---|---|---|---|
| KSD 1014 | ++ | ++ | ++ | ++ | ++ | ++ | ++ | ++ | ++ | ++ |
| JY 4306 | ++ | ++ | ++ | ++ | ++ | ++ | + | ++ | ++ | ++ |
| JY 4310 | ++ | + | ++ | ++ | ++ | ++ | − | − | − | − |
| JY 4285 | ++ | + | ++ | ++ | ++ | + | − | − | − | − |
| KSD 1500 | − | − | − | − | − | − | − | − | − | − |
| BC 100 | − | − | − | − | − | − | ++ | ++ | ++ | ++ |
| BC 207 | − | − | − | − | − | + | ++ | ++ | ++ | ++ |

MUCOSAL ADMINISTRATION OF PNEUMOCOCCAL ANTIGENS

REFERENCE TO RELATED APPLICATIONS

This application is a continuation-in-part of copending U.S. patent application Ser. No. 08/246,636 filed May 20, 1994, which itself is a continuation-in-part of copending U.S. patent application Ser. No. 08/048,896 filed Apr. 20, 1993, which itself is a continuation-in-part of copending U.S. patent application Ser. No. 07/835,698 filed Feb. 12, 1992, which itself is a continuation-in-part of U.S. patent application Ser. No. 07/656,773 filed Feb. 15, 1991 (now abandoned). The disclosure of such related applications are incorporated herein by reference.

FIELD OF THE INVENTION

This invention relates to mucosal immunization of animals with pneumococcal antigens to provide protection against pneumococcal colonization and systemic infection.

BACKGROUND TO THE INVENTION

*Streptococcus pneumoniae* causes more fatal infections world-wide than almost any other pathogen (refs. 1, 2,—a list of the references appears at the end of the disclosure). In the U.S.A., deaths caused by *S. pneumoniae* exceed in numbers those caused by AIDS (ref. 1). In the U.S.A., most fatal pneumococcal infections occur in individuals over 65 years of age, in whom *S. pneumoniae* is the most common cause of community-acquired pneumonia. In the developed world, most pneumococcal deaths occur in the elderly, or in immunodeficient patents including those with sickle cell disease. In the less-developed areas of the world, pneumococcal infection is one of the largest causes of death among children less than 5 years of age (refs. 3, 4, 5, 6). The increase in the frequency of multiple antibiotic resistance among pneumococci and the prohibitive cost of drug treatment in poor countries make the present prospects for control of pneumococcal disease problematical (refs. 7, 8, 9).

Humans acquire pneumococci through aerosols or by direct contact. Pneumococci first colonize the upper airways and can remain in nasal mucosa for weeks or months, As many as 50% or more of young children and the elderly are colonized. In most cases, this colonization results in no apparent infection (refs. 10, 11, 12). Studies of outbreak strains have suggested that even highly virulent strains, can colonize without causing disease (refs. 13, 14, 15, 16). These expectations have been recently confirmed using molecular probes to fingerprint individual clones (M. J. Crain, personal communication to one of the inventors). In some individuals, however, the organism carried in the nasopharynx can give rise to symptomatic sinusitis or middle ear infections. If pneumococci are aspirated into the lung, especially with food particles or mucus, they can cause pneumonia. Infections at these sites generally shed some pneumococci into the blood where they can lead to sepsis, especially if they continue to be shed into the blood in in large numbers. Pneumococci in the blood can reach the brain where they can cause meningitis. Although pneumococcal meningitis is less common than other infections caused by these bacteria, it is particularly devastating; some 10% of patients die and greater than 50% of the remainder have life-long neurological sequelae (refs. 17, 18).

In elderly adults, the present 23-valent capsular polysaccharide vaccine is about 60% effective against invasive pneumococcal disease with strains of the capsular types included in the vaccine (refs. 19, 20). The 23-valent vaccine is not effective in children less than 2 years of age because of their inability to make adequate responses to most polysaccharides (refs. 21, 22). Improved vaccines that can protect children and adults against invasive infections with pneumococci would help reduce some of the most deleterious aspects of this disease. A vaccine that protected against disease but did not reduce pneumococcal carriage rates would not, however, be expected to control the disease in immuno-compromised (ref. 20) and in unimmunized individuals. Such a vaccine would also not be expected to affect the rates of infection in immunized children prior to the development of an adequate anti-vaccine response.

A strategy that could control infections in all of these individuals would be any form of immunization that prevented or greatly reduced carriage, and hence transmission of pneumococci. In the case of immunization of young children with *Haemophilus influenzae* group b polysaccharide-protein conjugates, it has been observed that carriage is reduced from about 4% to less than 1%, (ref. 23), a possible explanation of concomitant herd immunity (ref. 24). If a vaccine could prevent colonization by pneumococci, such vaccine would be expected to prevent virtually all pneumococcal infections in the immunized patients. Since even unimmunized patients must acquire pneumococci from others, a vaccine that reduced carriage should reduce infections in immuno-compromised as well as unimmunized patients. In fact, an aggressive immunization program, coupled with antibiotic treatment of demonstrated carriers, might be able to largely eliminate the human reservoir of this organism. It may not be possible, however, to totally eliminate pneumococci since there are a number of reports that they have been found in laboratory rodents (ref. 25). Whether these pneumococci are infectious for man, easily transmittable to man, or even pathogens in wild rodents is not known. *S. pneumoniae* does not live free in the environment.

Although intramuscular immunization with capsular polysaccharide vaccines has been effective at reducing the incidence of pneumococcal sepsis in the elderly (ref. 20), it has not been reported to affect pneumococcal carriage rates in children up to 54 months of age (refs 26, 27). Whether the conjugate vaccine will reduce carriage in children is not known. Thus, the search for a vaccine with can reduce rates of nasopharyngeal carriage must include an examination of non-capsular antigens. Since immunity to carriage would be expected to operate at the mucosal surface, any attempt to identify antigens for vaccines against carriage should include immunizations designed to elicit mucosal immune responses. For these reasons, the present disclosure focuses on intranasal immunization with pneumococcal proteins in addition to the evaluation of polysaccharide-protein conjugates.

SUMMARY OF THE INVENTION

In accordance with the present invention, it has now been found that mucosal administration, particularly intranasally, of pneumococcal surface protein A (PspA) or an immunogenic fragment thereof provides protection to a host against pneumococcal colonization and systemic infection.

Accordingly, in one aspect, the present invention provides a method of protecting a host, particularly a human host, against colonization by pneumococci and systemic infection by mucosal administration, particularly by intranasal administration, to the host of an effective amount of at least one pneumococcal surface protein A and/or an immunogenic fragment thereof containing at least one protection-eliciting epitope.

The PspA may be in the form of killed whole *S. pneumoniae* or a lysate of whole *S. pneumoniae*. Alternatively, the PspA may be in the form of purified isolated protein or a fragment thereof. In a preferred aspect of the invention, the PspA is administered with cholera toxin B as an adjuvant.

In published International patent application WO 92/14488, which corresponds to the aforementioned U.S. Ser. No. 07/835,698, there are described the DNA sequences for the pspA gene from *S. pneumoniae* Rx1, the production of a truncated form of PspA by genetic engineering and the demonstration that such truncated form of PspA confers protection in mice to challenge with live pneumococci. The immunprotective truncated PspAs described in that publication may be used in the present invention for mucosal administration on the PspA fragments described above.

The ability of a vaccine to protect against pneumococcal colonization, as provided herein, means that the active component may protect against disease not only in the immunized host but, by eliminating carriage among immunized individuals, the pathogen and hence any disease it causes may be eliminated from the population as a whole.

In the date presented herein, it is shown that intranasal administration can also prevent sepsis resulting from intratracheal administration of pneumococci, so that the vaccine can protect against both pneumococcal colonization and sepsis.

GENERAL DESCRIPTION OF INVENTION

A principal determinant of specific immunity at mucosal surfaces in secretory IgA (S-IgA) which is physiologically and functionally separate from the components of the circulatory immune system. S-IgA antibody responses may be induced locally by the application of suitable immunogens to a particular mucosal site. The bulk of mucosal S-IgA responses, however, are the results of immunity generated via the common mucosal immune system (CMIS) (ref. 28), in which immunogens are taken up by specialized lymphoepithelial structures, collectively referred to as mucosa-associated lymphoid tissue (MALT). The best studied immunologic lympho-epithelial structures are the gut-associated lymphoid tissues (GALT), such as intestinal Peyer's patches. It is now clear, however, that other structurally and functionally similar lymphoid follicles occur at other mucosal surfaces, including those of the respiratory tract (ref. 29).

Bronchus-associated lymphoid tissue (BALT) was described by Bienenstock (refs. 30, 31) in experimental animals, but is apparently not present in the noninfected human bronchial tree (ref. 32). The upper respiratory tract in humans, however, is furnished with Waldeyer's ring of tonsils and adenoids. In rodents, the functional equivalent of these consists of nasal-associated lymphoid tissue (NALT), a bilateral strip of lymphoid tissue with overlying M-like epithelial cells at the base of the nasal passages (ref. 33).

In the experimental results set forth in the Examples below, it is shown that mice can be effectively immunized by intranasal (i.n.) instillation of bacterial protein immunogens, particularly when conjugated to or mixed with cholera toxin (CT) B subunit (CTB) (ref. 34). When CTB is used as an adjuvant for i.n. immunizations, specific IgA antibodies are induced in secretions of the intestinal, respiratory, and genital tracts, as well as predominantly IgA antibody-secreting cells in the intestinal lamina propria and salivary glands. Strong circulatory immune responses are also induced, with IgG and IgA antibodies in the serum, and IgG and IgA antibody-secreting cells in the spleen. The circulatory (or systemic) immune responses elicited by i.n. administration of antigens along with CTB are comparable with, or even stronger than, those induced by the administration of similar immunogens by the intragastric (i.g.; peroral) route (refs. 34, 35). Accordingly, it appears that i.n. immunization is an effective route for stimulating the CMIS as well as circulatory antibody responses.

Most soluble or non-replicating antigens are poor mucosal immunogens, especially by the peroral route, probably because they are degraded by digestive enzymes and have little or no tropism for the GALT. A notable exception is CT, which is a potent mucosal immunogen (ref. 36), probably because of the $G_{M1}$ ganglioside-binding property of its binding subunit, CTB, that enables it to be taken up by the M cells of Peyer's patches and passed to the underlying immunocompetent cells. In addition to being a good mucosal immunogen, CT is a powerful adjuvant (refs. 37, 38, 39). When administered in µg doses, CT greatly enhances the mucosal immunogenicity of other soluble antigens co-administered with it.

Purified cholera toxin subunit B (CTB) has also been shown to enhance mucosal immune responses (refs. 35, 41). Although it remains somewhat controversial, pure CTB probably does not have these properties when administered i.g. as an adjuvant. In the presence of very small amounts (<1 µg) of intact CT, however, CTB can act synergistically as a powerful oral adjuvant (ref. 40). This finding may account for apparent adjuvant activity of many commercial preparations of CTB that usually contain small amounts of contaminating CT. This direct adjuvant property of CTB is probably due to a targeting effect that promotes uptake of the CTB-antigen conjugate by M cells, and may be distinct from the adjuvant effect of co-administered CT (ref. 42). Although pure CTB does not act as an adjuvant when given i.g. in mice, it is strongly immunogenic when given orally to humans (refs. 43, 44).

In the experimental results contained in the Examples below, it is shown that CTB is a strong adjuvant when given i.n. in mice along with the pneumococcal protein, PspA. Although the inventors cannot completely rule out a role for small amounts of CT in these studies, CT was <0.1% of the 5 µg dose of CTB that was administered. Thus, it would appear that when administered i.n., CTB may be a stronger adjuvant and act more independently of CT, than when it is given i.g.

The mechanisms by which CT and CTB act as adjuvants are not fully understood, but are certainly complex, and appear to depend on several factors, including; 1) the toxic activity associated with the ADP-ribosylating property of the A1 subunit (ref. 45); 2) increased permeability of mucosae (refs. 46, 47), 3) enhanced antigen-presenting cell function (with increased levels of IL-1) (refs. 48, 49), as well as 4) direct stimulation of T and B cell activities (refs. 50, 51, 52, 53). This last point is controversial, however, as the in vitro effects of CT or CTB on T and B cells are generally inhibitory rather than stimulatory (refs. 54, 55, 56). Nevertheless, numerous reports attest to the in vivo mucosal immunoenhancing effects of CT and of CTB coupled to antigens (refs. 38, 39, 57, 58, 59, 60).

Although carriage of pneumococci can be maintained for long periods in the very young and the elderly, it is generally transient. Carriage is much less common in older children and young adults (refs. 10, 11, 12, 61, 62). One explanation for these findings is that carriage may be interfered with by immunity (possibly mucosal immunity) to pneumococci (refs. 11, 63). The inventors have shown that most human saliva have IgA antibodies to type 23 capsular polysaccharide and phosphocholine (an immunodominant determinant of pneumococcal cell wall teichoic acids (ref. 64)). It seems likely, therefore, that human sera would also contain antibodies to other pneumococcal antigens. In the case of group A streptococci, M proteins have been shown to be required for colonization in rats, and antibodies to M proteins can protect against colonization of the throat (refs. 65, 66).

Antibodies may be effective against carriage in two ways, namely; 1) they might act at the mucosal surface by opsonizing pneumococci or by blocking enzymes or toxins elaborated by the organism; 2) if nasopharyngeal carriage is dependent on minimal invasion of the nasal tissues, then protection against carriage might result from circulatory immunity that is released by inflammatory events. This latter mechanism may be evoked to explain the observation that carriage of H. influenzae can be prevented by an intramuscular vaccine (ref. 23). Another explanation of the effect of intramuscular immunization on carriage of H. influenzae are the recent observations that significant levels of antibody specific IgG and IgA are detected in secretions of children following immunization with the group b polysaccharide conjugate vaccine (refs. 24, 67).

Although definitive comparisons have not been made in most cases, existing mouse protection data (refs. 68, 69, 70, 71) suggests that antibodies that can opsonize pneumococci (e.g. those to the capsule) are generally more protective against sepsis than those that block the activities of toxins (e.g. pneumolysin) or enzymes (e.g. autolysin or neuraminidase). However, at the mucosal surface, the role played by antibodies that inactivate toxins and enzymes may be greater than that played by opsonic antibodies. The reason to suspect this is that for opsonic antibodies to exert their anti-bacterial effect, complement and phagocytes are required. Phagocytes are rare on the surface of normal nasopharyngeal tissue, and even if present, the phagocytes do not have the filtering action of the spleen and reticuloendothelial system to increase their chance of interactions with opsonized bacteria. Antibodies that block the virulence enhancing effects of pneumolysin and pneumococcal enzymes should able to bind their antigens just as effectively whether phagocytes were present or not.

The results provided herein show that i.n. immunization with heat-killed pneumococci and pneumococcal lysates, and purified PspA can protect mice against nasopharyngeal carriage. As noted earlier, the ability of a vaccine to protect against colonization means that it may protect against disease not only in the immunized host, but, by eliminating carriage among immunized individuals, the pathogen and hence any disease it causes may be eliminated from the population as a whole.

The vaccine composition which is administered intranasally as provided herein may be formulated in any convenient manner and in a dosage formulation consistent with the mode of administration and the elicitation of a protective response. The quantity of antigen to be administered depends on the subject to be immunized and the form of the antigen. Precise amounts and form of the antigen to be administered depend on the judgement of the practitioner. However, suitable dosage ranges are readily determinable by those skilled in the art and may be of the order of micrograms to milligrams. Suitable regimes for initial administration and booster doses also are variable, but may include an initial administration followed by subsequent administrations.

EXAMPLES

Example 1

This Example illustrates the provision of a model for pneumococcal carriage in mice.

Three different strains of S. pneumoniae (L82106, BG9163 and BG8826) were inoculated in 12 μl volumes into the nares of CBA mice over a period of several minutes using slow delivery from a 20 μl Pipetman. After 7 days, the mice were sacrificed and their trachea was cut at the top of the throat. 50 μl of fluid was instilled and washed out through the nares. The area washed represents the pharynx and nasal tissues. Each of these strains was able to establish carriage in this tissue without concomitant sepsis or bacteremia. The results are shown in the following Table I:

TABLE I

Carriage of three strains of S. pneumoniae in the naspopharnyx of CBA/N mice

| Strain Capsul Type $LD_{50}$ (i.v.) | L82106 6B $\geq 10^7$ | | BG9163 6B $-3 \times 10^3$ | | BG8826 23F $\geq 10^7$ | |
|---|---|---|---|---|---|---|
| Mouse | #1 | #2 | #1 | #2 | #1 | #2 |
| Nasal | 6,561 | 1,422 | 1,494 | 3,267 | 31,733 | 10,093 |
| Blood | <3 | <3 | <3 | <3 | <3 | <3 |
| Lungs | 600 | <60 | <60 | <60 | <60 | 180 |

Note: mice were inoculated with the indicated numbers of CFU i.n. and sacrificed 8 days later. Data expressed as CFU in the 50 μl nasal wash, in the 1 ml of lung homogenate, or in 50 μl of blood. Infection of CBA/N mice i.p. with $10^7$ L82016 is invariably fatal.

After the first day after infection, it was also observed some low numbers of pneumococci in the lung and blood of occasional mice. Later in the infections, pneumococci were only recovered from the nasal wash. Colonization appeared to be stable for at least 3 weeks, as shown by the result in the following Table II.

TABLE II

CFU recovered from the nasopharnyx of mice infected i.n. with $10^8$ strain L82106

| | Experiment #1 (day and mouse #) | | | | | | Experiment #2 (day and mouse #) | | | | | |
|---|---|---|---|---|---|---|---|---|---|---|---|---|
| | Day 1 | | Day 3 | | Day 6 | | Day 14 | | | Day 19 | | |
| Source | #1 | #2 | #1 | #2 | #1 | #2 | #1 | #2 | #3 | #1 | #2 | #3 |
| Nasal Wash | 56,862 | 5,346 | 29,160 | 6,336 | 41,365 | 9,504 | 202 | <3 | 261 | 67 | 760 | 124 |
| Blood | <20 | 1,782 | <20 | <20 | <20 | <20 | <3 | <3 | <3 | <3 | <3 | <3 |
| Lungs | <20 | 1,920 | <20 | <20 | <20 | <20 | n.d. | n.d. | n.d. | n.d. | n.d. | n.d. |

Note: Data expressed as CFU in the 50 μl nasal wash, in the 1 ml of lung homogenate, or in 50 μl of blood. Since mice were killed to obtain the nasal wash, different mice were done at each time point.

To identify the pneumococci from nasal washes, they were plated on gentamicin plates since this antibiotic does not kill pneumococci but kills most other bacterial from the nose (ref. 72). Individual colonies from each nasal wash were then picked and replated with an optochin disk to confirm that they were pneumococci. In some cases, the bacteria were capsule-typed to be sure that they were, in fact, the same bacteria with which inoculated the mice were innoculated. Control mice that received no bacteria yielded no bacteria that grew on 0.02% gentamicin and were sensitive to optochin. Subsequent studies have shown that challenge with as few as $2 \times 10^7$ also yields carriage in all mice. Lower doses down to $10^3$ yield comparable carriage in most mice but as many as ¼ to ⅓ of the mice fail to carry any pneumococci after 1 week. These studies indicate that the ideal dose is probably between $10^7$ and $10^8$ CFU of L82016.

Example 2

This Example illustrates elicitation of protection against carriage by immunization with heat killed pneumococci and with a lysate of pneumococci.

CBA mice were immunized i.n. with $2 \times 10^7$ heat-killed (60° C.) L82016 or an equal number of autolysed L82016. Mice were given three i.n. immunizations spaced 10 days apart. The first two injections were given with 5 μg of CTB. Two weeks after the last injection the mice were challenged with $10^8$ CFU of live L82016. The results obtained are set forth in the following Table III:

TABLE III

Elicitation of protection against carriage by immunization with heat killed and autolysed pneumococci

| Immunogen | CFU from individual mice | Geometric mean CFU | P vs CTB | P vs none |
|---|---|---|---|---|
| Heat Killed L82016 + CTB | <3, <3, 3, 9, 26 | 4.8 | <.01 | <.02 |
| Autolysed L82016 + CTB | <3, <3, <3, 8, 30 | 4.5 | <.01 | <.02 |
| CTB | 9, 160, 197, 248, 741 | 139 | n.s. | n.s. |
| None | 6, 1340, >1400*, >1400* | >354 | n.s. | n.s. |

*Dead, value assigned > 1400 for calculationn
P values calculated by Student's t-test.
n.s. = not significantly different.

Example 3

This Example illustrates protection against carriage by immunization with isolated and purified PspA.

CBA/N mice at 10 weeks of age were immunized with 12 μl of a solution of L82016 PspA (containing about 1 μg PspA) plus 5 μg of CTB, or a control preparation from PspA⁻ strains WG44.1 (also with 5 μg of CTB). This preparation was used to control for the possibility that some pneumococcal contaminant other than PspA might have elicited the protection seen. The PspA used was purified over a choline-Sepharose column. Other controls included mice immunized with CTB alone and unimmunized mice. Two of the control mice died of pneumococcal sepsis following challenge with $10^8$ L82016. The other control mice all had detectable pneumococci in their nasal washes 7 days post infection. None of the PspA immunized mice had any pneumococci in their nasal washes at 7 days post infection. Of the 7 surviving control mice, all of which carried pneumococci in their nasal cavity, only two showed pneumococci in the blood 7 days post infection. Thus, for the 5 others, it is clear that the pneumococci in the nasal cavity were there because of colonization and not because of generalized pneumococcal sepsis.

The data is presented in the following Table IV:

TABLE IV

Elicitation of protection against carriage by immunization with isolated PspA

| Immunogen | CFU from individual mice | Geometric mean CFU | P vs PapA⁻ | P vs pooled controls |
|---|---|---|---|---|
| FL-L82016 PspA + CTB | <3, <3, <3 | <3 | 0.028 | <0.0001 |
| PspA⁻ (WG44.1) + CTB | 128, 18,277, 49, 527 | 4,875 | — | — |
| CTB | 1,059, 26,720, dead¹ | 11,226 | — | — |
| None | 426, 11,484, dead¹ | 6254 | — | — |

P values calculated by Welch's t-test. n.s. = not significantly different.
¹for the purpose of the statistical calculations these two mice were assigned carriage values of 50,000 since 49,000 was the highest carriage level observed in a live animal.

Example 4

This Example illustrates elicitation of protection against intratracheal challenge by intranasal immunization with PspA.

Full-length PspA was recovered from *S. pneumoniae* R36A strain (which provides the same PspA as the Rx1 strain). The strain was grown in chemically-defined medium (Rijn et al, Infect. & Immun. 1990, vol. 27, pp 444–448), except that the medium contained 0.03% choline chloride. The bacteria were harvested in late log phase (about $5 \times 10^7$ CFU/ml) and washed five times with 20 ml of saline followed by centrifugation at 2000×g for 10 minutes. With each wash, the bacteria were saved and the supernatant discarded. The washed cells then were eluted with 5 ml of 2% choline chloride and the eluted material was shown to contain PspA by dot blot using monoclonal antibody XiR 278.

An identical procedure was carried out on the *S. pneumoniae* strain WG44.1 (McDaniel et al (III)), which does not produce PspA because of the absence of an upstream portion of the pspA gene. This material provided a control, in that the preparation should contain the same general impurities that might be in the extract from R36A. The material recovered from the washed WG44.1 cells by elution with 2% choline chloride did not contain detectable PspA by dot blot, as expected.

For the purpose of administration, the PspA preparation from R36A was diluted ½. 12 μl of the solution contained 5 μg of added cholera toxin B subunit (CTB) as an adjuvant and was instilled into the nose of each BALB/cJ mouse. Thirty-two and forty-two days later the immunization was repeated in an identical manner. As a control, some mice were immunized with an identical preparation from the WG44.1 *S. pneumoniae* strain. A final group was left unimmunized. Seven days after the third dose, the immunized mice were challenged with $2 \times 10^6$ CFU ($100 \times LD_{50}$) of A66 *S. pneumoniae* intratracheally.

Activity assays also were performed on sera obtained seven days after the third immunization on separate groups of mice immunized by protocols almost identical to those noted above.

The results obtained are set forth in the following Table V:

TABLE V

Intranasal Immunization with R36A PspA
and
Intratracheal Challenge with Capsular Type 3 Strain A66

| Immunogen | Adjuvant | IgG anti-PspA (μg/ml) | Challenge CFU of A66 | CFU/ml at day 3 | Day of Death |
|---|---|---|---|---|---|
| FL-PspA⁻* (R3GA) | CTB | 17.8 ± 3.3 | 2 × 10⁶ " " " | <10² <10² <10² <10² | >12** >12 >12 >12 |
| PspA⁻ (WG44.1) | CTB " " " | <0.4 | 2 × 10⁶ " " " | 2 × 10⁸ 4 × 10⁵ 4 × 10⁴ 2 × 10⁴ | 3 4 4 4 |
| Saline " " " | Saline " " " | ≦0.4 | 2 × 10⁶ " 2 × 10⁵ " | N.D. N.D. N.D. N.D. | 4 4 4 5 |

**FL-PspA vs. Saline (or WG44.1) at P < .005
*FL-Pspa = full length Pspa
*PspA (WG44.1) = preparation containing no PspA, prepared from a mutant strain which does not produce PspA As can be seen in Table IV, 24 hours after infection the unimmunized and the mock immunized mice had high levels of pneumococci in their blood. These mice all died on day 3 post challenge. The mice immunized with PspA exhibited no detectable pneumococci on day 3 and all survived infection. Although the data in Table V clearly indicate that i.n. immunization with PspA can protect against pulmonary challenge, the strain of S. pneumoniae used, survives well in blood and causes rapid death in mice when injected i.v. ($LD_{50} < 10^2$). Thus, the protection against death may have been due to protection against sepsis rather than being an indication that protection had been elicited in the lung.

BRIEF DESCRIPTION OF DRAWINGS

FIG. 3 is the DNA sequence of the pspA gene with deduced amino acid sequence for the PspA protein;

FIG. 4 depicts the restriction map of pspA (FIG. 4A) and the use of insertion-duplication mutagenesis to construct mutations in the pspA gene (FIG. 4B), FIG. 5 shows the deduced amino acid sequence for the N-terminal region of PspA and the general location of epitopes recognized by monoclonal antibodies;

FIG. 6 shows antibody reactivity with PspA fragments produced by various pspA gene segments.

GENERAL DESCRIPTION

According to one aspect of the present invention, there is provided a purified immunoprotective pneumococcal surface protein, comprising a truncated form of PspA which contains the immunoprotective epitopes of the protein and up to about 90% of the whole PspA protein and from which the functional cell membrane anchor region is absent.

Through the technique of insertion-duplication mutagenesis of the pspA gene of the strain Rx1 of Streptococcus pneumoniae with plasmids containing cloned fragments of the pspA structural gene, it has been possible to produce soluble fragments of PspA that are secreted by pneumococci.

In another aspect of the present invention, therefore, there is provided a method of forming an immunoprotective truncated PspA protein, which comprises effecting insertion-duplication mutagenesis of a bacterium with a pspA gene resulting in the coding of a truncated expressible PspA protein, growing the mutated bacterium to effect expression of a truncated PspA protein, and isolating the protein.

The molecular size of the purified truncated PspA protein obtained may be varied by directing the point of insertion, which determines the termination of gene expression, to different points in the pspA gene. For example, an N-terminal fragment of apparent molecular weight of 43 kD, constituting approximately one-half of the native protein, has been found useful.

The truncated segment which is produced by this procedure is capable of eliciting protection in mice from fatal challenge with type 3 S. pneumoniae, demonstrating for the first time that a purified PspA can elicit protection and that this truncated segment of the protein contains protective epitopes of PspA.

Figures 1, 2:
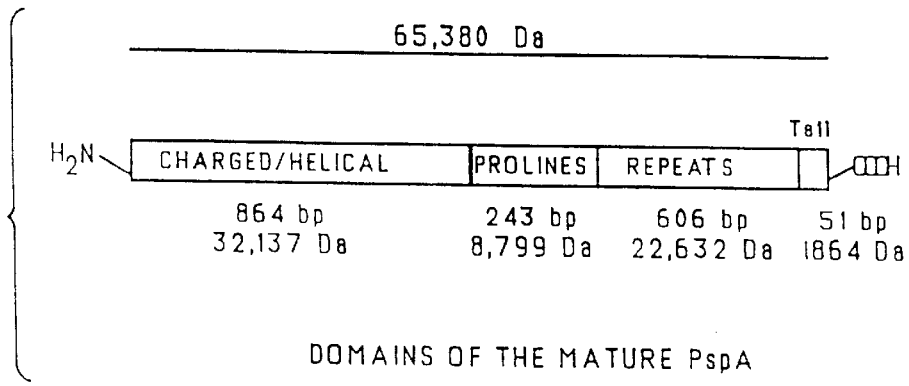
FIG. 1 is a schematic representation of the domains of the mature PspA.
FIG. 2 is the N-terminal amino acid sequence of PspA, wherein bold upper case letters denote charged hydrophilic amino acids, lower-case letters designate apolar, hydrophobic residues, and underlined bold lower case letters denote uncharged, polar, hydrophilic residues.

Amino acid sequence information was obtained on the N-terminal 45 amino acids of the truncated segment of PspA. This sequence is shown in FIG. 2. Predictive secondary structural analysis shows that this sequence has a very strong alpha-helical formation, with no non-helical inserts. About 51% of the segment is composed only of two amino acids, namely lysine, a charged amino acid, and alanine, a non-polar amino acid.

Analysis of this 45-amino acid sequence also reveals that it contains a seven-residue periodicity (see FIG. 2). In PspA, the periodicity begins with residue 8 and extends throughout the entire sequence, for nearly eleven turns of the helix. Positions "a" and "d" are occupied by apolar amino acids and position "b", "c" and "f" generally contain hydrophilic amino acids. Position "f" is predominantly occupied by lysine. Having regard to these observations, this region of PspA is very likely in an alpha-helical coiled-coil configuration. The deduced amino acid sequence for the whole of the α-helical coiled-coil region is shown in FIG. 5.

Figure 3A:
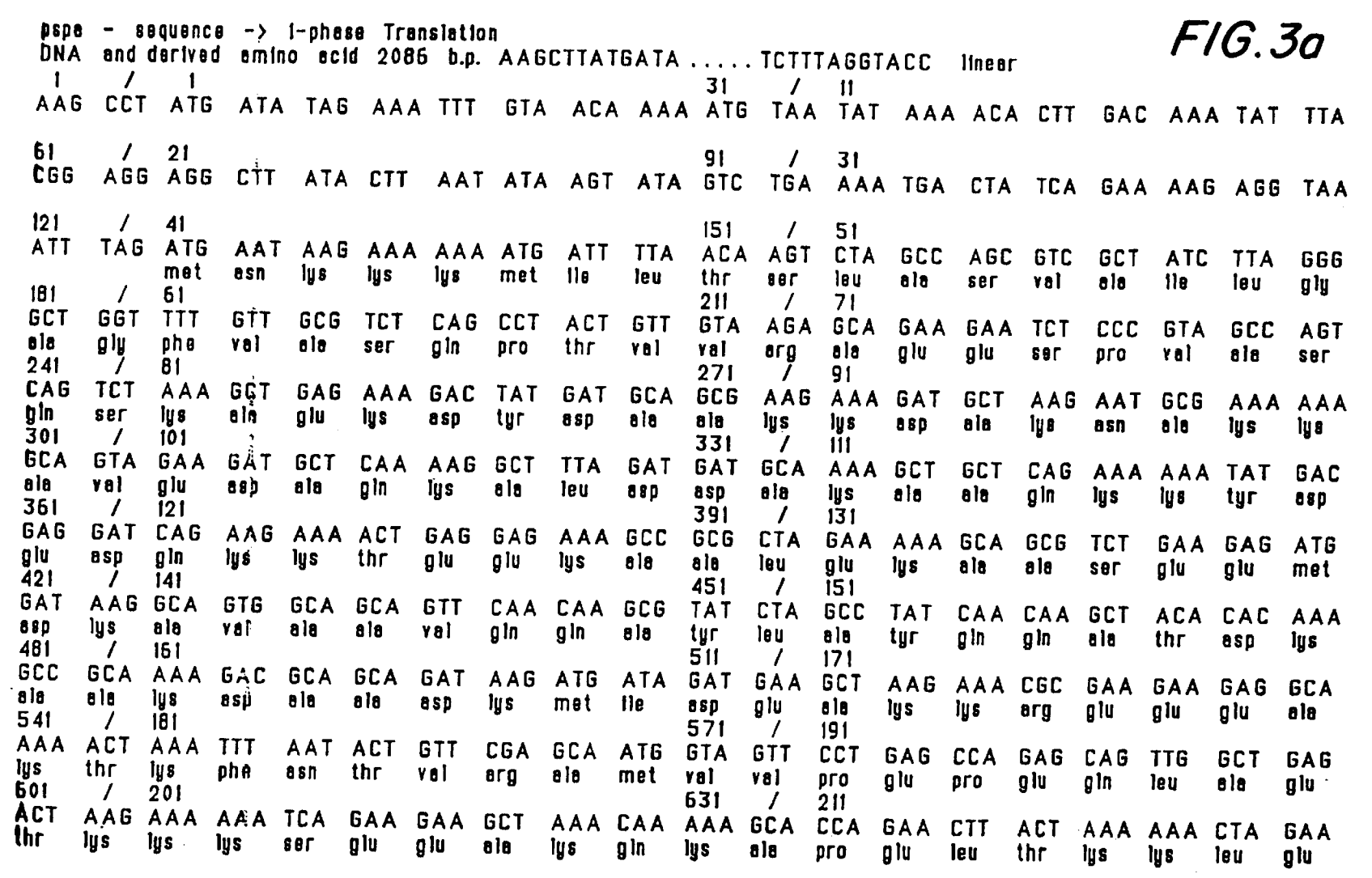
Figure 3B:
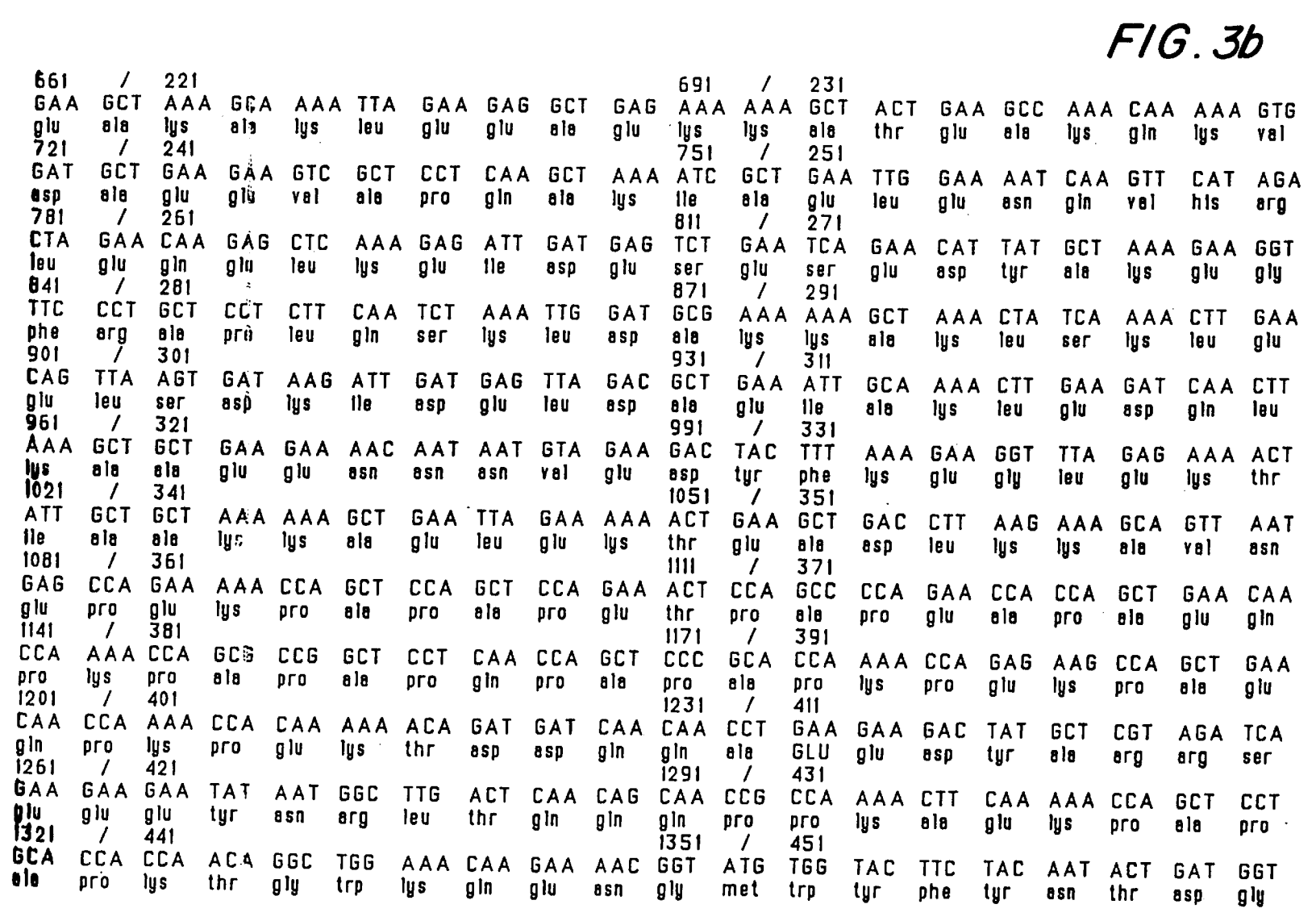

We also have cloned and sequenced the entire coding region of pspA (see FIG. 3). The deduced amino acid sequence for the PspA protein reveals three distinct regions of the PspA molecule, shown schematically in FIG. 1. Accordingly, a further aspect of the present invention, there is provided a biologically-pure recombinant DNA molecule coding for the PspA protein or portions thereof and having a coding sequence included within set forth in FIG. 3 or having substantial homology thereto.

The DNA sequence of the pspA gene is contained on a HindIII-KpnI fragment that is 2086 base pairs in length. The pspA gene itself represents approximately 1985 base pairs of this fragment, and comprises an initial region containing transcription and translational signals with translation starting at the ATG/met (nucleotide position 127, codon position −31), followed by a leader sequence extending from the AAG/met (nucleotide position 127, codon position −31) to CGA/ala (nucleotide position 217, codon −1). Mature Pspa starts with the glu amino acid at nucleotide position 220 (codon +1) and ends at the translational stop TAA/OCH at nucleotide position 1984. This translational stop codon is followed by transcription termination signals.

The amino terminal of the protein sequence, predicted from the DNA sequence of FIG. 3, contains a 31 amino acid leader sequence and a 45 amino acid sequence identical to the 45 amino acid sequence of the N-terminal of PspA (FIG. 2). The amino end of the predicted protein sequence is highly charged and α-helical in nature. This region has homology with tropomyosin at the amino acid level (approximately 22% identity and 50% similarity). This homology is due largely to a repeating seven residue periodicity where the first and fourth amino acids are hydrophobic, the intervening amino acids are helix-promoting and the seventh amino acid is charged. This pattern is consistent with that of an α-helical coiled-coil molecule and indicates that the α-helical coil extends through the N-terminal half of the molecule. The amino acid sequence of the whole of the α-helical coil region is shown in FIG. 5.

Following the charged helical region is a proline-rich region in which 23 of 81 amino acids are prolines. Immediately carboxy to the proline-rich region is the first of ten highly homologous twenty amino acid repeats. The only significantly hydrophobic region in the sequenced portion of the molecule begins at the last repeat. This potential membrane-spanning region contains several charged amino acids preceding the translational stop codon.

The insertionally-inactivated mutants of S. pneumoniae lacking the C-terminal anchor regions are capable of growth in chemically-defined medium and secrete the N-terminal portion of the PspA protein into the medium. The N-terminal region of PspA is highly soluble in the culture medium and is much easier to isolate than the entire molecule. Soluble truncated molecules have been produced using insertional duplicational mutagenesis directed by the cloned PspA DNA fragments shown in FIG. 4. Expression of the same truncated construct (with the pneumococcal promoter) in E.coli results in the same PspA fragment being secreted into the periplasm of E.coli. PspA is readily released from the periplasm by hypotonic lysis.

Truncated PspA is isolated from culture medium of mutant pneumococci in any convenient manner, such as by tangential flow filtration. Ion-exchange chromatography then is performed on an anionic resin to purify the protein. In this procedure, the solution containing PspA is dialyzed to pH6 in 0.02 M salt solution and passed over the resin. The PspA is eluted from the resin with a gradient of 0.08 to 2.0 M ionic strength and is collected in the fraction between 0.34 and 0.87 M ionic strength, depending on the nature of the column used.

The PspA may be further purified by sodium dodecyl sulfate polyacrylamide gel (SDS-PAGE) electrophoresis. The PspA-containing portion of the gel is identified by staining of the gel and PspA is electroeluted from this portion.

The electrophoresis purification is convenient when only small quantities of PspA are being handled. As an alternative, more suited to large-scale production, the protein may be purified by size chromatography in a pH7 phosphate buffer.

Since it is possible to obtain expression of the truncated form of PspA into the culture medium, as opposed to it being trapped within the cell wall and making purification much more complicated, it is possible to isolate other proteins that have been cloned into the truncated pspA gene by making fusion proteins between PspA and other proteins. Such a technique may be employed to enhance the immunogenicity or preserve the immunogenic structural conformation or presentation of the gene product, to permit the fusion protein to be used in immunization, which may be systemic and/or mucosal, against disease.

One example of such a fusion protein is a fusion of the soluble N-terminal region of PspA and the B-subunit of cholera toxin. Fusion proteins also may be formed by chemical attachment of the truncated PspA protein to other proteins.

Another aspect of the present invention, therefore, provides a method for the production of cloned proteins, which comprises fusing a pspA gene coding for a truncated form of PspA protein with the gene coding for another protein to form a fusion protein clone, transforming S.pneumoniae, E.coli or other bacteria with the fusion protein clone, growing the transformed bacterium to effect expression of a fusion protein comprising truncated PspA and the other protein into the culture medium, and isolating the fusion protein.

By using this technique, there can be produced cloned proteins in gram positive bacteria, such as pneumococci, for example, *S.pneumoniae,* and mycobacteria, for example, Bacille Calmette-Guerin (BCG). This approach overcomes the problems inherent in the production of proteins in gram negative bacteria, such as *E. coli,* usually used for cloning, in particular the need to purify the recombinant proteins from endotoxin and the toxicity of many gram positive DNA sequences in gram negative organisms.

For the expression of a fusion protein comprising the soluble N-terminal region of PspA and the B-subunit of cholera toxin (CTB), a gene fusion of a pspA gene coding for a truncated form of PspA protein with a ctxB gene coding for the B-subunit of cholera toxin is effected. Following expression of the fusion protein, the PspA and CTB may be cleaved one from another by dilute acid at an asparagine-proline sequence, known to be labile to dilute acid, engineered at the fusion site of the two proteins.

CTB is known to be highly specific for monosinloganglioside ($G_{M1}$). Accordingly, the fusion PspA-CTB protein may be isolated from the culture medium by adsorption to a $G_{M1}$ affinity column, from which the fusion protein subsequently may be eluted at low pH.

The PspA-CTB fusion protein finds considerable utility in solid phase immunoadsorbant assays. By using the fusion protein, it is possible to coat solid supports, such as microtitration plates, with PspA fragments without having first to isolate the PspA fragments. This may be done by adding bacterial extract containing the fusion protein to plates coated with $G_{M1}$. The PspA-CTB fusion protein then binds to $G_{M1}$ through the CTB moiety, thereby coating the solid support with PspA. The resulting coated product then may be used in a solid phase immunoadsorbant assay for the detection of PspA antibody and/or antigen in test samples. Such immunoadsorbant assays constitute an additional aspect of this invention.

The PspA attachment/anchor region, containing the proline-rich region, the repeat region and/or the C-terminus of PspA, also may be employed to effect expression of heterologous proteins in pneumococci, or other gram positive or gram negative bacteria in the which the attachment/anchor region is functional. Generally, expression is effected on bacterial membrane, cell walls or cell surfaces in gram positive bacteria and in the periplasm of gram negative bacteria. An example of such heterologous protein is the B-subunit of cholera toxin.

As mentioned above, the truncated form of PspA provided herein contains the immunoprotective epitopes of the protein and hence is useful in a vaccine against pneumococcal infection. Accordingly, a yet further aspect of the present invention provides a vaccine against pneumococcal infection comprising, as an immunogenically-active component, the purified immunoprotective pneumococcal surface protein provided herein. The PspA protein may be employed as one component of a multicomponent vaccine which is effective in providing protection from a variety of infections.

In addition, gram positive bacteria which have been transformed to express the pspA gene coding for the truncated soluble PspA protein may be employed, in a live-attenuated or killed form, as an immunologically-active component of a vaccine against pneumococcal infection. In the transformed bacterium, such pspA gene may be fused to a gene coding for another protein. Accordingly, an additional aspect of this invention provides a vaccine against pneumococcal infection comprising, as an immunologically-active component, a live-attenuated or killed bacteria containing a gene coding for the truncated form of PspA.

The truncated form of PspA also may be employed in conjugates with normally weakly-immunogenic or non-immunogenic protection-eliciting molecules, such as various polysaccharides, to achieve immunogenic potentiation thereof. An additional aspect of the invention, therefore, provides a vaccine comprising, as an immunogenically-active component, a conjugate of the purified immunoprotective pneumococcal surface protein provided herein and a normally weakly-immunogenic or non-immunogenic protection-eliciting molecule.

Conserved sequences of pspA, particularly those in the proline-rich and/or repeat regions of the gene, may be employed as probes to detect the presence of pneumococci of various strains, through detection of pneumococcal DNA, in tissues, body fluids and/or secretions. Similarly, portions of the pspA gene may be used in diagnostic kits for the detection of pneumococcal infections.

In addition, primers made based on conserved sequences of pspA, particularly those in the proline-rich and/or repeat regions, may be used to assay for the presence of pneumococci in tissues, body fluids and/or secretions, through amplification of pneumococcal DNA. In this regard, a single primer pair derived from the nucleotide sequence of the pspA gene of S.pneumoniae may be employed in an assay using the polymerase chain reaction (PCR) for the specific detection of Streptococcus pneumoniae.

Specific amplification has been achieved of a 678 base pair DNA fragment from S.pneumoniae strain Rx1. After 30 cycles of amplification, the amplimer was detectable by agarose gel electrophoresis. The fragment was successfully amplified in all 32 strains of S.pneumoniae tested. PCR DNA amplification was able to detect less than an estimated 20 ficograms total genomic pneumococcal DNA.

Primers LSM1 and LSM2, having the nucleotide sequences.
LSM1 (SEQUENCE ID NO: 5)
5'-CCGGATCCAGCTCCTGCACCAAAAC-3'
LSM2 (SEQUENCE ID NO: 6)
5'-GCGCTGCGACGGCTTAAACCCATTCACCATTGG-3' amplified the 678 base pair product from pspA from nucleotides 1312 to 1990 of the Rx1 pspA sequence (FIG. 3).

The PCR analysis using the primers described herein is performed in accordance with conventional PCR techniques, such as are described in the literature, for example, as described in Arnhem et al at C&EN Special Report, 36, Oct. 1, 1990. For detection purposes, the primer may be labelled or labelled nucleotide triphosphates may be included in the PCR reaction to label the PCR amplification product.

The PCR primers may be prepared by well-known methods, for example, by oligonucleotide synthesis or by fragmentation of a larger nucleotide sequence using suitable restriction enzymes.

The ability to use a single primer capable of detecting a large number of S.pneumoniae strains enables a universal PCR detection kit to be provided which is able to diagnose pneumococcal infection in mammals, including humans, independent of the strain which has caused the disease.

Example 5.1

This Example illustrates the preparation and growth of novel strains of S. pneumoniae.

The S. pneumoniae strain Rx1, which is a non-encapsulated derivative of capsular type 2 strain D39 (National Collection of Type Cultures, London, NCTC #7466), was subjected to insertional inactivation (as described in McDaniel et al (III) 1987, Crain et al 1990, Talkington et al 1991, with 10 different cloned fragments of PspA (see FIG. 4). These fragments have all been obtained from restriction digests of cloned PspA DNA on a plasmid in E.coli strain JY4313 (deposited with the American Type Culture Collection on Jan. 31, 1991 under ATCC accession number 68529). This insertional duplication mutagenesis (see FIG. 4) results in the termination of gene expression near the 3' end of the cloned fragment.

One of the resultant strains, JY2008 (deposited with the American Type Culture Collection on Jan. 24, 1991 under accession number 55143), which was produced by a fragment of DNA encoded in pKSD300 (McDaniel et al (III) 1987), produces a PspA fragment of 27 kDa (apparent molecular weight 43 kDa). This fragment is approximately 40% the size of the native 65 kDa (84 kDa apparent size) protein.

The expected molecular size is based on the deduced amino acid sequence and the apparent molecular size is based on migration in SDS-PAGE. The difference between expected and apparent molecular size is due to the conformation of the PspA fragment.

The proline and repeats/anchor regions (see FIG. 1) were deleted and the resulting protein was unable to attach to cell due to their absence. The unattached protein then may be isolated from culture supernatants, as described below.

Figure 7:
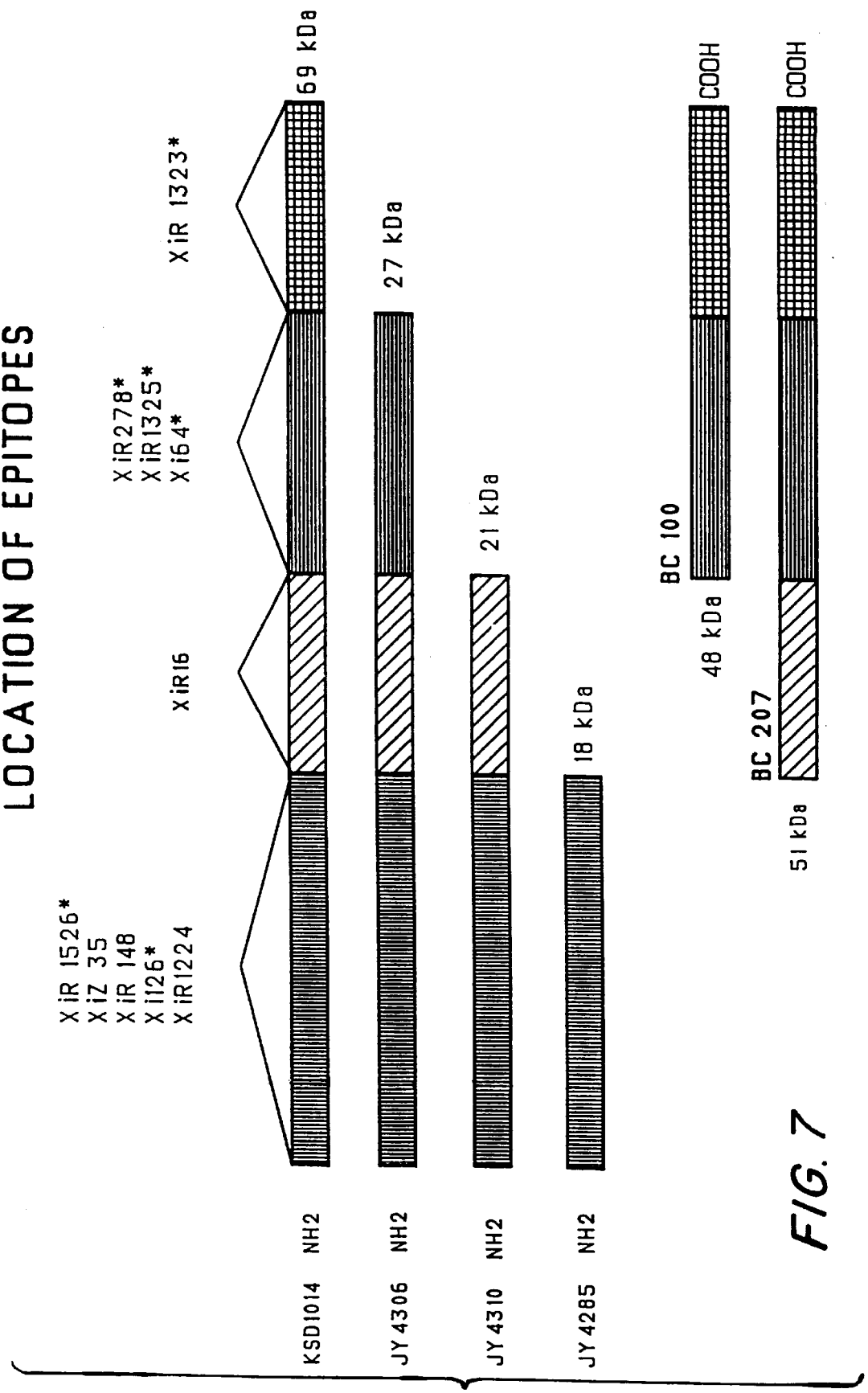
FIG. 7 shows the mapped location of epitopes in the PspA fragments produced by the different pspA gene segments.

By directing the insertion to different points in the pspA gene, different lengths of truncated, non-attached PspA protein derivatives can be produced, as seen in FIG. 7.

STRAINS. PLASMIDS AND PROBES

In the Examples which follow as well as in the accompanying drawings, reference is made to certain plasmids and bacterial strains transformed by such plasmids as well as vector DNA segments, some of which have been deposited with ATCC and all of which are fully described herein. The following Table 5.II provides a summary of such materials.

TABLE 5.II

| Identification | Type | Description | Deposit | Location |
|---|---|---|---|---|
| JY4313 | E. coli strain | PspA DNA | ATCC 68529 | FIG. 1 |
| JY2008 | S. pneumoiniae strain | PspA fragment 43 kDa | ATCC 55143 | FIG. 1 |
| JY4306 | E. coli strain | PspA fragment 43 kDa | ATCC 68522 | FIG. 3 |
| JY4310 | | PspA fragment 21 kDa | None | FIG. 7 |
| JY4285 | | PspA fragment 18 kDa | None | FIG. 7 |
| pJY4163 | Plasmid | Expression plasmid used for expression of PspA -CTB fusion protein (29 kDa) | None | FIG. 6 |
| JY4323 | DNA probe | HindIII-KpaI segment | None | FIG. 8 |
| JY4306 | DNA probe | HindIII-Dra-I segment | None | FIG. 8 |
| JY4262 | DNA probe | BclI-Bst-NI segment | None | FIG. 8 |

The pneumococcal strain JY2008 was grown in 6 liters of a chemically defined medium (see Inf. Imm. 27:444) supplemented with 0.10% choline chloride, 0.075% L-cysteine hydrochloride and 0.25% NaHCO$_3$. The supernatant fluid of the mid-log phase culture of JY2008 was harvested using a 0.22 $\mu$m membrane tangential flow filter and concentrated 60 fold.

Introduction of the plasmid pKSD300 into the unmodified D39 strain similarly yielded the 43 kD truncated PspA protein. Introduction of the plasmid pKSD300 into the type 3 S.pneumoniae strain WU2 (PspA protein approximately 92 kD) yielded, upon growth of the organism, a non-attached truncated PspA protein of approximately 46 kD molecule size.

Example 5.2

This Example illustrates the purification of PspA.

The concentrated supernatant fluid, produced as described in Example 1, was washed in 0.1 M PBS, pH 7.2, and ultracentrifuged at 196,000 xg. The supernatant fluid was diluted 1:5 in 20 mM L-histidine buffer-NaCl, the pH adjusted to 6.0 and the injected into a DEAE-fibered Isonet-D2 an ion exchange column.

A stepwise NaCl gradient from 80 mM to 2 M was applied to the column and PspA-containing fractions (0.32 to 0.64 M ionic strength) were pooled and separated on an SDA-polyacrylamide gel. The proteins on a representative section of the gel were stained with Comassie Blue R-250 to identify PspA. The fraction containing PspA was excised from the remainder of the SDS-gel and electroeluted from the excised gel. The eluted protein was precipitated in a 50:50 methanol:acetone solvent and resuspended in PBS. Purity of product was confirmed by silver staining and Western Immunoblotting with mAb Xi126 (IgG 2b, k, see McDaniel et al (I), supra).

Example 5.3

This Example illustrates the isolation of PspA from the periplasmic space of Escherichia coli.

Isolation from the periplasmic space of E. coli was accomplished by standard techniques. E. coli strain JY4306 (which produces the 43 kDa N-terminal fragment of PspA, the amino acid sequence of which is shown in FIG. 3. This strain was deposited with ATCC on Jan. 31, 1991 under accession number 68522) was washed in buffered saline, incubated in 20% sucrose, 10 mM EDTA, 25 mM Tris pH 7.7 for 10 minutes at 0° C. The cells then were spun at 400 xg for 10 minutes at 0° C. All supernatant was removed from the pellet and the pellet was resuspended rapidly in about 100 volumes of 4° C. water. After 10 minutes the suspension was centrifuged at 4,000 xg for 10 minutes at 4° C. The pellet was discarded and the supernatant, which contained the PspA was saved. Concentration of the supernatant was by standard procedures such as concentration against solid sucrose or ultrafiltration. Purification of the protein isolated from E. coli proceeded by the same chromatography techniques used for the isolated of the 43 kDa (truncated) PspA from the media of growing pneumococci.

Example 5.4

This Example illustrates the immunogenic properties of the PspA protein.

Sixteen 7-week old CBA/N mice carrying the Xid mutation (Jackson Laboratories, Bar Harber, Me.) were bled via the periorbital sinus to establish pre-exposure levels of antibody to PspA. Purified PspA, prepared as described in Example 5.2, was emulsified in complete Freund's adjuvant and injected subcutaneously into the inguinal and axillary regions, delivering approximately 5 $\mu$g of protein per mouse. Fourteen days later, the mice were injected intraperitoneally with 5 $\mu$g of PspA, prepared as described in Example 2. Control mice were immunized via the same routes with sterile SDS buffer. Seven days after the last immunization, all mice were bled via the periorbital sinus and were challenged intravenously with 300 CFU of the type 3 strain WU2, grown as described in Example 5.1.

Preimmunization and prechallenge sera were analyzed by Western immunoblots to establish baseline and postimmunization response to the truncated protein. The PspA of strain WU2 was electrophoresed and transferred to nitrocellulose membranes. The membranes were separated into strips and probed with the appropriate mouse antisera at a 1:50 dilution for 2 hours, incubated with biotinylated goat anti-mouse immunoglobulin for 1 hr, washed and incubated with Strepavidin-conjugated phosphatase. The membranes were developed with 5-bromo-4-chloro-3-indoyl phosphate toludine salt with 0.01% into blue tetrazolium.

Of the eight CBA/N mice immunized with the purified fragment of PspA, all were still alive 14 days after challenge with strain WU2 and none showed any signs of illness following challenge. Of the eight mice immunized with buffer controls, six were dead by two days post challenge, while the two remaining control mice appeared very sick, with ruffled fur, arched back and decreased movement, two to three days following challenge but survived. Chi-square analysis indicated that there was a significant difference ($P<0.003$) in survival between the immunized and control groups.

Preimmunization and prechallenge sera were analyzed by Western immunoblotting. None of the preimmunization sera contained antibody to truncated PspA. Postimmunization sera from eight of eight mice contained detectable antibodies to PspA, and six mice had very strong anti-PspA reactions. When the challenge strain WU2 was probed with the antisera, all the immunized mice had antibodies that were highly cross-reactive with the WU2 PspA epitopes. No control mice developed antibodies to PspA.

The immunization data is summarized in the following Table 5.III:

TABLE 5.III

| Immunogen | Detection of Antibody to PspA | Alive at 2 days post challenge | Alive at 14 days post challenge |
|---|---|---|---|
| Isolated PspA (Example 2) | 8/8 | 8/8 | 8/8 |
| Sterile SDS (control) | 0/8 | 2/8 | 2/8 |

As may be seen from the data in Table III, immunization with two 5 µg doses of the purified PspA molecule elicited protection against fatal infection of CBA/N mice and elicited antibodies reactive with the PspA of the challenge strain.

Example 5.5

This Example illustrates sequencing of the PspA protein.

Purified PspA, prepared as described in Example 5.2, was electrophoresed through 9% resolving gels containing recrystallized SDS with the Laemmli buffer system (Nature 227:680). The gels were soaked twice in a 10 mM 3-(cyclohexylamino)-1-propanesulfonic acid, pH 11.0, containing 10% methanol for 10 minutes. A polyvinylidene difluoride membrane (PVDF) was wetted completely for several seconds in 100% methanol, then washed in CAPS buffer for 10 min. PspA was electrotransferred to the PVDF membrane in CAPS buffer at 0.5 A for 1 hr. After transfer, the membrane was washed two times in deionized water for 5 min, and stained with 0.1% Coomassie Blue R-250 in 50% methanol for 20 minutes. The section of the membrane containing PspA was excised and destained in 40% methanol and 10% acetic acid for 5 min. The membrane was cut into small segments and stored in sterile Eppendorf tubes until sequencing.

The isolated PspA was sequenced directly from the PVDF membranes. FIG. 2 depicts the N-terminal 45 residue amino acid sequence and FIG. 5 depicts the amino acid sequence for the whole alpha-helical region. The DNA sequence of the whole pspA gene and the deduced amino acid sequence for the PspA protein are shown in FIG. 3.

Example 5.6

This Example illustrates the use of the pspA 5'-sequence and/or the PspA N-terminal region to serve as an expression and leader sequence for expressing and/or excreting/secreting heterologous proteins from S.pneumoniae and E.coli. In this Example, there is described the expression of the N-terminal of the PspA protein fused to the B-subunit of cholera toxin (CTB) through a genetic fusion and the excretion of the fused protein from pneumococci and its secretion into the periplasmic space of E.coli.

A fusion protein consisting of CTB and the N-terminal half of PspA was constructed and expressed in E.coli. The HindIII/DraI pspA gene fragment used contained all the pspA transcription and translation initiation signals and the PspA signal peptide leader sequence for transport across the cell membrane. The mature PspA encoded by this fragment is predicted to be a product of 29 kDa (observed molecular weight of 42 kDa), encompassing more than 90% of the α-helical coiled-coil domain. The CTB fragment used lacked transcription and translation initiation signals. Expression from pspA promoter through pspA and then in-frame translational readthrough into the CTB-encoding gene ctxB resulted in production of a 12 kDa CTB product fused to the upstream PspA product. The PspA-CTB fusion protein was stably expressed in both high and low copy number plasmids (pUC18, more than 100 copies/cell; pJY4163, about 15 to 30 copies/cell) in E.coli.

The fusion products were of the expected size (about 54 kDa) and reacted with antibody to both PspA and CTB. That the CTB product retained its functionality was demonstrated by the ability of the fusion protein to bind ganglioside $G_{M1}$, a property of CTB.

The high level of expression of the fusion product apparently resulted in a reduced rate of processing and/or conformational changes that prevented the protein from being completely transported to the periplasm. However, in the lower copy number construct, about 60% of the fusion protein was localized in the periplasm, where large quantities were readily released from E. coli by osmotic shock.

In addition to expression in E.coli, the fusion protein also was expressed in S.pneumoniae by transformation of the low copy number construct into the avirulent S.pneumoniae Rx1 to generate an insertion-duplication mutant. In this way, the gene encoding the fusion protein was integrated into the S.pneumoniae chromosome, from which it was stably expressed. As in the case of Example 1, the truncated PspA molecule lacking the attachment/anchor region, this time in the form of the PspA-CTB fusion protein, was excreted into the culture supernatant. The fusion protein product was of the expected molecular size (54 kDa), reacted with antibody to PspA and CTB, and bound $GM_1$.

Example 5.7

This Example illustrates the use of PspA attachment or anchor region to permit expression of heterologous proteins on the surface of S.pneumoniae or other bacteria in which the attachment/anchor sequence is functional in particular the expression of a PspA-CTB (cholera toxin B subunit) fusion expressed on the surface of pneumococci.

The N-terminal encoding region of PspA, including its transcription and translation initiation signals and its signal peptide leader sequence, is linked via a translationally in-frame genetic fusion to the CTB-encoding ctxB fragment that lacks transcription and translation initiation and termination signals. This sequence is followed in-frame by the PspA attachment/anchor domain, including part or all of the proline, repeat and C-terminal domains. The resulting fusion protein is directed to the outside of the cell via the PspA leader sequence, which is cleaned following transport across the membrane, and then attached to cell by the PspA attachment/anchor sequence. The heterologous protein, located between the two PspA fragments is expressed on the outside surface of the membrane and, in S.pneumoniae, on the surface of the cell.

Example 5.8

This Example illustrates the expression of truncated and full length PspA by the Mycobacterium tuberculosis strain Bacille Calmette-Guerin (BCG).

BCG was chromosomically modified to incorporate the pspA gene coding for the truncated PspA protein. The 43 kDa truncated PspA protein was expressed from the modified BCG to approximately 15% of total BCG protein. This result was achieved with an expression vector construct carrying the pspA gene segment encoding the 43 kDa region without its 5'-secretion signal. Expression was only about 1% of BCG protein when the PspA or mycobacterial signal sequences were included. In either case, a significant portion of the expressed PspA was excreted into the medium. Expression of the 43 kDa PspA protein in a fusion with the mycobacterial lipoprotein signal sequence resulted in the expression of the recombinant PspA in the membrane fraction of BCG.

This latter result suggested that the fusion of the lipoprotein signal sequence resulted in acylation of the recombinant PspA. Fluorescent activated cell sorting with fluorochrome-conjugated monoclonal antibodies to PspA demonstrated expression of PspA on the surface of these bacteria.

Example 5.9

This Example illustrates the close homology of portions of the pspA gene among different strains of pneumococci and the potential that such homology may be useful for molecular (DNA) approaches to detect pneumococci in tissues, body fluids and/or secretions and to identify pneumococci grown from patient samples.

Three DNA probes were employed, namely full length pspA, JY4323 (N-terminal HindIII to C-terminal KpnI), the N-terminal half of pspA, JY4306 (N-terminal HindIII to DraI at position 996 (see FIG. 3) and most of the proline and repeat regions, JY4262 (BclI at position 1221 to BstNI at position 1832). Under stringency conditions requiring 95% identity, probes JY4323 and JY4262 reacted with cells of over 200 independent isolates of *S.pneumoniae* by Southern blot.

When the chromosomal DNA was cut with HindIII, there generally was observed that each of these probes detected two discrete bands whose exact size was dependent on the strain examined. In Rx1 pneumococci, the two bands were 4.0 and 9.1 kb. The 4.0 kb band corresponded to pspA and was altered or absent in pspA mutants. The other band shares some homology with the coding regions for both the N-terminal and C-terminal halves of PspA but is not affected by pspA mutations. The JY4323 and JY4262 probes failed to react with another gram positive bacterium, *Streptococcus pyogenes,* and a gram negative bacterium, *Salmonella typhimurium.* The N-terminal probe, JY4306, recognized about one-third of the strains of pneumococci tested.

These results indicate that a sequence included in the proline/repeat region is shared by all strains of pneumococci and apparently not by other bacterial species. Sequences in the N-terminal half of the molecule appear to be more variable.

Example 5.10

This Example illustrates the detection and determination of the location of epitopes in the α-helical N-terminal region of PspA.

Monoclonal antibodies protective against pneumococcal infection in a mouse model, denoted by an asterisk in FIGS. 5, 6 and 7, were used to determine the location of epitopes for each antibody in the α-helical N-terminal region of PspA. The sites were mapped to fragments of PspA. The results are illustrated in FIGS. 5 to 7, with FIG. 5 showing the deduced amino acid sequence for the N-terminal region of PspA and the general location of epitopes recognized by monoclonal antibodies, FIG. 6 showing antibody reactivity with PspA fragments produced by various pspA gene segments, and FIG. 7 showing the mapped location of epitopes in the PspA fragments produced by the different pspA gene segments.

Numbers 138, 193 and 261 in FIG. 5 indicate break positions in the PspA fragments used to map the location of epitopes detected by monoclonal antibodies Xi1526, Xi126, XiR35, XiR38, XiR1224, XiR16, Xi64, XiR278, Xi1325 and Xi1323. The asterisk (*) after some of the antibodies denotes those which are able to protect against fatal pneumococcal infection with strain WU2 pneumococci.

In addition, the vertical lines to the right of the Figure indicate those areas predicted to have coiled-coil α-helical structure. The divisions to the left of the Figure indicate the mapped location of the epitopes for each antibody.

SUMMARY OF DISCLOSURE

In summary of this disclosure, the present invention relates to a truncated PspA molecule capable of eliciting an immunoprotective response and hence containing the protective epitopes of PspA protein. Modifications are possible within the scope of this invention.

SEQUENCE LISTINGS

Submitted with this application are Sequence Listings, identified as follows:

(a) SEQ ID No: 1 shows the nucleotide sequence and derived amino acid sequence for the HindIII-KpnI fragment containing the complete pspA gene, as shown in FIG. 3.

(b) SEQ ID No: 2 shows the derived amino acid sequence for the PspA protein, as shown in FIG. 3.

(c) SEQ ID No: 3 shows the N-terminal amino acid sequence of PspA, as shown in FIG. 2.

(d) SEQ ID No: 4 shows the derived amino acid sequence for the N-terminal region of PspA as shown in FIG. 5.

(e) SEQ ID No: 5 shows the nucleotide sequence for primer LSM1.

(f) SEQ ID No: 6 shows the nucleotide sequence for primer LSM2.

SUMMARY OF THE DISCLOSURE

In summary of this disclosure, the present invention provides a method of preventing colonization of pneumococci in a host and for protecting against systemic infection by pneumococci, by mucosal, particularly intranasal (intranasopharyngeal), administration of PspA in various forms. Modifications are possible within the scope of the invention.

Example 8

This Example shows cross-protection of an animal model against challenge by a variety of virulent pneumococcal strains by recombinant PspA fragments.

Five mice were immunized with purified PspA fragment produced by pBC207 (produced as described in Example III) in *E. coli* and five with PspA purified fragment produced by pBC100 (produced as described in Example III)in *E. coli.* In both cases, the fragments were injected in Freund's Complete Adjuvant, boosted two weeks later with the fragment in saline and challenged 7 days post boost. All mice immunized with each fragment survived challenge with 100×$LD_{50}$ of WU2 capsular type 3 *S.pneumoniae.*

Five additional mice were injected with adjuvant plus an equivalent preparation of non-PspA producing *E. coli*. All mice died when challenged with the same dose of WU2 strain.

In addition, further numbers of mice were immunized with purified fragment produced by pBC100 in *E. coli* following the protocol described above. The mice were challenged with a variety of virulent strains and the pBC100 fragment was found to protect mice against 7 of 14 virulent strains and to extend life for the other 7 strains. The results obtained, which includes the result for the WU2 challenge, are set forth in the following Table V:

TABLE VI

Protection Mediated by Recombinant (BC100)
(amino acids 192–588) PspA from strain Rx1

| Challenge strain | Serotype | | Alive:Dead | | Median Day of Death | |
|---|---|---|---|---|---|---|
| | Caps | PspA | BC100 (rPspA) | none | BC100 (rPspA) | none |
| D39 | 2 | 25 | 0:5 | 0:3 | 5 | 2 |
| WU2 | 3 | 1 | 4:0 | 0:3 | >21* | 3 |
| A66 | 3 | 13 | 4:0 | 0:3 | >21* | 1 |
| EF10197 | 3 | 18 | 5:0 | 0:3 | >21* | 2 |
| ATCC6303 | 3 | 7 | 5:0 | 0:5 | >21** | S |
| EF5668 | 4 | 12 | 1:3 | 0:3 | 9.5 | 4 |
| EF3296 | 4 | 20 | 1:3 | 0:3 | 5 | 3 |
| L81905 | 4 | 23 | 1:5 | 0:6 | 5* | 2.5 |
| BC9739 | 4 | 26 | 0:4 | 0:3 | 7 | 2 |
| DBL5 | 5 | 33 | 0:5 | 0:3 | 5* | 2 |
| BG7322 | 6 | 24 | 4:0 | 1:3 | >21* | 6 |
| EF6796 | 6A | 1 | 4:0 | 0:3 | >21* | 1 |
| DBL6A | 6A | 19 | 5:0 | 0:3 | >21* | 7 |

*, different from "none" at $P < .004$ in one tailed tests, **, different from "none" at $P < .05$ one tailed tests, all are Fisher exact except DBLS and LB1905 where the one tailed two sample rank test was used.

Further, additional mice were immunized with a purified PspA fragment (BAR 416) produced by *E. coli* and corresponding to amino acids 192 to 260, following the protocol described above and challenged with various strains of *S. pneumoniae* against which protection was provided by the pBC100-derived fragment. The results obtained are contained in the following Table VI:

TABLE VII

Protection Mediated by Recombinant BAR416
(amino acids 192–260) PspA from strain Rx1

| Challenge strain | Serotype | | Alive:Dead | | Median Day of Death | |
|---|---|---|---|---|---|---|
| | Caps | PspA | BAR416 (rPspA) | none | BAR416 (rPspA) | none |
| WU2 | 3 | 1 | 4:1 | 0:4 | >21 | 3 |
| A66 | 3 | 13 | 5:0 | 0:5 | >21 | 2 |
| BG7322 | 6B | 24 | 3:2 | 0:4 | >21 | 7 |
| ATCC6303 | 3 | 7 | 5:0 | 0:5 | >21 | 5 |
| EF6796 | 6A | 1 | 3:2 | 0:5 | >21 | 5 |
| DBL6A | 6A | 19 | 5:0 | 0:S | 7 | 2 |

The strains tested are all strains protected against by immunization with BC100. The results indicate that the region from 192–260 is able to elicit much of the cross-protection elicited by BC100.
Infected with $\geq 100 \times LD_{50}$ of each strain. In all cases this is $\geq 10^3$ CFU.

As may be seen from this Table VI, protection was afforded against challenge in many instances and in others the life was extended.

The data presented in this Example conclusively proves that epitopes C-terminal to amino acids 119 and 192 respectively are capable of eliciting protective immunity. This result is consistent with the findings presented in the earlier Examples that the region of PspA from amino acids 192 to 260 contains at least one protection-eliciting epitope.

REFERENCES

1. Anonymous. Centers for Disease Control HIV/AIDS Serveillance Report. 1991; August :1–18.
2. Fraser D W. What are our bacterial disease problems. In: J B Robbins, Hill J C, Sadoff J C ed. Bacterial Vaccines. New York; 1982: xix–xxiv.
3. Berman S, McIntosh K. Selective primary health care: stratagies for control of disease in the developing world. XXI acute respiratory infections. Rev. Infect. Dis, 1985; 7: 647–491.
4. Greenwood B M, Greenwood A M, Bradley A K, Tulloch S, Hayes R, Oldfield F S J. Deaths in infancy and early childhood in a well vaccinated, rural, West African population. Ann, Trop. Pediatr. 1987; 7: 91–99.
5. Spika J S, Munshi M H, Wojtyaniak B, Sack D A, Hossain A, Rahman M, Saha S K. Acute lower respiratory infections: a major cause of death in children in Bangladesh. Ann. Trop. Pediatr. 1989; 9: 33–39.
6. Bale J R. Etiology and epidemiology of acute respiratory tract infections in children in developing countries. Rev. Infect. Dis. 1990; 12 (Suppl 8): S861–S1083.
7. Munoz R, Musser J M, Crain M, Briles D E, Marton A, Parkinson A J, Sorensen U, Tomasz A. Geographic distribution of penicillin-resistant clones of *Streptococcus pneumoniae*: characterization by penicillin-binding protein profile, surface protein A typing, and multilocus enzyme analysis. Clinic. Infect. Dis. 1992; 15: 112–118.
8. Marton A, Gulyas M, Munoz R, Tomasz A. Extremely high incidence of antibiotic resistance in clinical isolates of *Streptococcus pneumoniae* in Hungary. J. Infect. Dis. 1991; 163: 542–548.
9. Klugman K P. Pneumococcal resistance to antibiotics. Clin. Microbiol. Rev. 1990;
10. Gray B M, Converse G M III, Dillon H C. Epidemiologic studies of *Streptococcus pneumoniae* in infants: acqusition, carriage, and infection during the first 24 months of life. J. Infect. Dis. 1980; 142: 923–933.
11. Gray B M, Converse G M III, Huhta N, Johnston R B Jr., Pichichero M E, Schiffman G, Dillon H C Jr. Antibody response to pneumococcal carriage. J. Infect. Dis. 1981; 142: 312–318.
12. Hendley J O, Sande M A, Stewart P M, al. e. Spread of *Stereptococcus pneumoniae* in families. I. Carriage rates and distribution of types. J. Infect. Dis. 1975; 132: 55.
13. Smillie W G, Warnock G H, White H J. A study of a type I pneumococcus epidemic at state hospital at Worchester Massachusettes. Am J Pub Hlth 1938; 28: 293–302.
14. Smillie W G. A study of an outbreak of type II pneumococcal pneumonia in the Veterans Administration Hospital at Bedford, Mass. Am. J. Hyg. 1936; 24: 522–535.
15. Gratten M, Naraqi S, Hansman D. High prevalence of penicillin-insensitive penumococci in port moresby, Paupa New Guinea. Lancet 1980; ii: 192–195.
16. DeMaria T F, McGhee R B, Lim D J. Rheumatoid factor in otitis media with effusion. Arch. Otolaryngol. 1984; 110: 279–280.
17. Bohr V, Rasmussen N, Hansen B, Gade A, Kjersem H, Johsen N, Paulson O. Pheumococcal meningitis: An evaluation of prognostic factors in 164 cases based on mortality and on a study of lasting sequelae. J. Infect. Dis. 1985; 10: 143–157.
18. Klein J O. The epidemiology of pneumococcal diseases in infants and children. Rev. Infect. Dis. 1981; 3: 246–.

19. Bolan G, Broome C V, Facklam R R, Plikaytis B D, Fraser W D, Schlech W F I. Pneumococcal vaccine efficacy in selected populations in the Unites States. Ann. Intern. Med. 1986; 104: 1–6.

20. Shapiro E D, Berg A T, Austrian R, Schroeder D, Parcells V, Margolis A, Adair R K, Clemmens J D. Protective efficacy of polyvalent pneumococcal polysaccharide vaccine. N. Engl. J. Med 1991; 325: 1453–1460.

21. Cowan M J, Ammann A J, Wara D W, Howie V M, Schultz L, Doyle N, Kaplan M. Pneumococcal polysaccharide immunization in infants and children. Pediatrics 1978; 62: 721–727.

22. Gotschlich E C, Goldschneider I, Lepow M L, Gold R. The immune response to bacterial polysaccharides in man. Antibodies in human diagnosis and therapy. New York: Raven, 1977: 391–402.

23. Barbour M L, Mayon-White R T, Crook D W, Coles C, Moxon E R. The influence of *Haemophilus influenzae* type b (Hib) conjugate vaccine (PRP-T) on oropharyngeal carriage of Hib in infants under 12 months of age. ICAAC Abstracts 1993; 33: 175.

24. Chiu S S, Greenberg P D, Marcy S M, Wong V K, Chang S J, Chiu C Y, Ward J I. Mucosal antibody responses in infants following immunization with *Haemophilus influenzae*. Pediatric Res. Abstracts 1994; 35: 10A.

25. Fallon M T, Reinhard M K, Gray B M, Davis T W, Lindsey J R. Inapparent *Streptococcus pneumoniae type 35* infections in commercial rats and mice. Laboratory Animal Science 1988; 38: 129–.

26. Douglas R M, D H, Miles H B, Paton J C. Pneumococcal carriage and type-specific antibody Failure of a 14-valent vaccine to reduce carriage in healthy children. American Journal of Diseases of Children 1986; 140: 1183–1185.

27. Douglas R M, Miles H B. Vaccination against *Streptococcus pneumoniae* in childhood: lack of demonstrable benefit in young Australian children. Journal of Infectious Diseases 1984; 149; 861–869.

28. Mestecky J. The common mucosal immune system and current strategies for induction of immune response in external secretions. J. Clin. Immunol. 1987; 7: 265–276.

29. Croitoru K, Bienenstock J. Characteristics and functions of mucosa-associated lymphoid tissue. In: P L Ogra, Mestecky J, Lamm M E, Strober W, McGhee J R, Bienenstock J ed. Handbook of Mucosal Immunology. San Diego, Calif.: Academic Press, Inc., 1994: 141–149.

30. Bienenstock C, Johnston N, Perey D Y. Bronchial lymphoid tissue. I. Morphologic characteristics. Lab. Invest. 1973; 28: 686–692.

31. Bienenstock J, Johnston N, Perey D Y. Bronchial lymphoid tissue. II. Functional characterisitics. Lab. Invest. 1973; 28: 693–698.

32. Pabst R. Is BALT a major component of the human lung immune system? Immunology Today 1992; 13: 119–122.

33. Kuper C F, Koornstra P J, Hameleers D M H, Biewenga J, Spit B J, Duijvestijn A M, van Breda Vriesman P J C, Sminia T. The role of nasopharyngeal lymphoid tissue. Immunol. Today 1992; 13: 219–224.

34. Wu H-Y, Russell M W. Induction of mucosal immunity by intranasal application of a streptococcal surface protein antigen with the cholera toxin B subunit. Infection and Immunity 1993; 61: 314–322.

35. Russell M W, Wu H-Y. Distribution, persistence, and recall of serum and salivary antibody responses to peroral immunization with protein antigen I/II of *Streptococcus mutans* coupled to the cholera toxin B subunit. Infection and Immunity 1991; 59: 4061–4070.

36. Elson C O, Ealding W. Generalized systemic and mucosal immunity in mice after mucosal stimulation with cholera toxin. J. Immunol. 1984; 132: 2736–2741.

37. Elson C O. Cholera toxin and its subunits as potential oral adjuvants. Curr. Topics Microbiol. Immunol. 1989; 146: 29–33.

38. Lycke N, Holmgren J. Strong adjuvant properties of cholera toxin on gut mucosal immune responses to orally presented antigens. Immunology 1986; 59: 301–308.

39. Wilson A D, Stokes C R, Bourne F J. Adjuvant effect of cholera toxin on the mucosal immune response to soluble proteins. Differences between mouse strains and protein antigens. Scand, J. Immunol. 1989; 29; 739–745.

40. Wilson A D, Clarke C J, Stokes C R. Whole cholera toxin and B subunit act synergistically as an adjuvant for the mucosal immune response of mice to keyhole limpet haemocyanin. Scand. J. Immunol. 1990; 31: 443–451.

41. Czerkinsky C, Russell M W, Lycke N, Lindblad M, Holmgren J. Oral administration of a streptococcal antigen coupled to cholera toxin B subunit evokes strong antibody responses in salivary glands and extramucosal tissues. Infect. Immun. 1989; 57: 1072–1077.

42. Holmgren J, Lycke N, Czerkinsky C. Cholera toxin and cholera B subunit as oral-mucosal adjuvant and antigen vector systems. Vaccine 1993; 11: 1179–1184.

43. Quiding M, Nordström I, Kilander A, Anderson G, Hanson L A, Holmgren J, Czerkinsky C. Intestinal immune responses in humans. Oral cholera vaccination induces strong intestinal antibody responses and interferon-λ production and evokes local immunological memory. J. Clin. Invest. 1991; 88: 143–148.

44. Svennerholm A M, Jertborn M, Gothefors L, Karim A M M M, Sack D A, Holmgren J. Mucosal antitoxin and antibacterial immunity after cholera disease and after immunization with a combined B subunit-whole cell vaccine. J. Infect. Dis. 1984; 149: 884–893.

45. Lycke N, Tsuji T, Holmgren J. The adjuvant effect of *Vibrio cholerae* and *E. coli* heat labile enterotoxins is linked to the ability to stimulate cAMP, European Journal of Immunology 1992; 22: 2277–2281.

46. Lycke N, Karlsson U, Sjölander A, Magnusson K-E. The adjuvant action of cholera toxin is associated with an increased intestinal permeability for luminal antigens. Scandinavian Journal of Immunology 1991; 33: 691–698.

47. Gizurarson S, Tamura S, Kurata T, Hasiguchi K, Ogawa H. The effect of cholera toxin and cholera toxin B subunit on the nasal mucosa membrane. Vaccine 1991; 9: 825–832.

48. Bromander A, Holmgren J, Lycke N. Cholera toxin stimulates IL-1 production and enhances antigen presentation by macrophages in vitro. Journal of Immunology 1991; 146: 2908–2914.

49. Anastassiou E D, Yamada H, Francis M L, Mond J J, Tsokos G C. Effects of cholera toxin on human B cells. Cholera toxin induces B cell surface DR expression while it inhibits anti-$\mu$ antibody-induced cell proliferation. J. Immunol. 1990; 145: 2375–2380.

50. Muñoz E, Zubiaga A M, Merrow M, Sauter N P, Huber B T. Cholera toxin discriminates between T helper 1 and 2 cells in T cell receptor-mediated activation: Role of cAMP in T cell proliferation. J. Exp. Med. 1990; 172: 95–103.

51. Lycke N, Strober W. Cholera toxin promotes B cell isotype differentiation. J. Immunol. 1989; 142: 3781–3787.

52. Wilson A D, Bailey M, Williams N A, Stokes C R. The in vitro production of cytokines by mucosal lymphocytes immunized by oral administration of keyhole limpet hemocyanin using cholera toxin as an adjuvant. European Journal of Immunology 1991; 21: 2333–2339.

53. Francis M L, Ryan J, Jobling M G, Holmes R K, Moss J, Mond J J. Cyclic AMP-independent effects of cholera toxin on B cell activation. II. Binding of ganglioside $G_{M1}$ induces B cell activation. Journal of Immunology 1992; 148: 1999–2005.
54. Woogen S D, Ealding W, Elson C O. Inhibition of murine lymphocyte proliferation by the B subunit of cholera toxin. Journal of Immunology 1987; 139: 3764–3770.
55. Garrone P, Banchereau J. Agonistic and antagonistic effects of cholera toxin on human B lymphocyte proliferation. Molecular Immunology 1993; 30: 627–635.
56. Haack B M, Emmrich F, Resch K. Cholera toxin inhibits T cell receptor signaling by covalent modification of the CD3-ζ subunit. Journal of Immunology 1993; 150: 2599–2606.
57. Abraham E, Robinson A. Oral immunization with bacterial polysaccharide and adjuvant enhances antigen-specific pulmonary secretory antibody response and resistance to pneumonia. Vaccine 1991; 9: 757–764.
58. Szu S C, Li X, Schneerson R, Vickers J H, Bryla D, Robbins J B. Comparative immunogenicities of Vi polysaccharide-protein conjugates composed of cholera toxin or its B subunit as a carrier bound to high- or lower-molecular-weight Vi. Infect. Immun. 1989; 57: 3823–3827.
59. Chen K-S, Strober W. Cholera holotoxin and its B subunit enhance Peyer's patch B cell responses induced by orally administered influenza virus: disproportionate cholera toxin enhancement of the IgA B cell response. Eur. J. Immunol. 1990; 20: 433–436.
60. Liang X, Lamm M E, Nedrud J G. Oral administration of cholera toxin-Sendai virus conjugate potentiates gut and respiratory immunity against Sendai virus. Journal of Immunology 1988; 141: 1495–1501.
61. Brimblecombe F S W, Cruicshank R, Masters P L, Reid D D, Stewart G T. Family studies of respiratory infections. British Medical Journal 1958; : 119–128.
62. Masters P L, Brumfitt W, Mendez R L, Likar M. Bacterial flora of the upper respiratory tract in Paddington families, 1952–1954. Brit. Med. J. 1958; 1: 1200–1205.
63. Gwaltney J M, Sande M A, Austrian R, al. e. Spread of *streptococcus pneumoniae* in families: II Relation of transfer of *Streptococcus pneumoniae* to incidence of colds and serum antibody. J. Infect. Dis. 1975; 132: 62.
64. Russell M W, Prince S J, Ligthart G J, Mestecky J, Radl J. Comparison of salivary and serum antibodies to common environmental antigens in elderly, edentulous, and normal adult subjects. Aging Immunol. Infect. Dis. 1990; 2: 275–286.
65. Bessen D, Fischetti V A, Influence of intranasal immunization with synthetic peptides corresponding to conserved epitopes of M protein on mucosal immunization by group A streptococci. Infect. Immun. 1988; 56: 2666–2672.
66. Hollingshead S K, Simecka J W, Michalek S M. Role of M protein in pharyngeal colonization by group A streptococci in rats. Infect. Immun. 1993; 61: 2277–2283.
67. Kauppi M, Eskola J, Kathty H. H. influenzae type b (Hib) conjugate vaccines induce mucosal IgA1 and IgA2 antibody responses in infants and children. ICAAC Abstracts 1993; 33: 174.
68. Briles D E, Forman C, Horowitz J C, Volanakis J E, Benjamin W H Jr., McDaniel L S, Eldridge J, Brooks J. Antipneumococcal effects of C-reactive protein and monoclonal antibodies to pneumococcal cell wall and capsular antigens. Infect. Immun. 1989; 57: 1457–1464.
69. Briles D E, Claflin J L, Schroer K, Forman C. Mouse IgG3 antibodies are highly protective against infection with *Streptococcus pneumoniae*. Nature 1981; 294: 88–90.
70. Lock R A, Paton J C, Hansman D. Comparative efficacy of pneumococcal neuraminidase and pneumolysin as immunogens protective against *Streptococcus pneumoniae*. Microb. Pathog. 1988; 5: 461–467.
71. Lock R A, Hansman D, Paton J C. Comparative efficacy of autolysin and pneumolysin as immunogens protecting mice against infection by *Streptococcus pneumoniae*. Microbial Pathogenesis 1992; 12: 137–143.
72. Converse G M III, Dillon H C Jr. Epidemiological studies of *Streptococcus pneumoniae* in infants: methods of isolating pneumococci. J. Clin. Micro. 1977; 5: 293–296.

---

What we claim is:

1. A method for eliciting an immunological response in a host susceptible to pneumococcal carriage, which method consists essentially of mucosally administering to the host an immunizing amount of a composition consisting essentially of (i) pneumococcal surface protein A (PspA) isolated from a pneumococcal strain or a fragment of such PspA containing a protection-eliciting epitope; and optionally (ii) an adjuvant.

2. A method for eliciting an immunological response in a host susceptible to pneumococcal carriage, which method consists essentially of mucosally administering to the host an immunizing amount of a composition consisting essentially of (i) heat killed whole pneumococci; and optionally (ii) an adjuvant.

3. A method for eliciting an immunological response in a host susceptible to pneumococcal carriage, which method consists essentially of mucosally administering to the host an immunizing amount of a composition consisting essentially of (i) a lysed pneumococci; and optionally (ii) an adjuvant.

4. The method of claim 1 wherein said adjuvant is present in the composition and is the B subunit of cholera toxin.

5. The method of claim 2 wherein the adjuvant is present in the composition and is the B subunit of cholera toxin.

6. The method of claim 1 wherein said mucosal administration is effected intranasally.

7. A method for eliciting an immunological response in a host susceptible to pneumococcal carriage against colonization of *Streptococcus pneumoniae* in the nasopharnyx, which method consists essentially of intranasally administering to the host an immunizing amount of a composition consisting essentially of (i) pneumococcal surface protein A (PspA) isolated from pneumococci; and (ii) optionally an adjuvant.

8. The method of claim 7 wherein the adjuvant is present in the composition and is the B subunit of cholera toxin (CTB).

9. The method of claim 3 wherein the adjuvant is present in the composition and is the B subunit of cholera toxin.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 2086 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
AAGCTTATGA TATAGAAATT TGTAACAAAA ATGTAATATA AAACACTTGA CAAATATTTA      60

CGGAGGAGGC TTATACTTAA TATAAGTATA GTCTGAAAAT GACTATCAGA AAAGAGGTAA     120

ATTTAGATGA ATAAGAAAAA AATGATTTTA ACAAGTCTAG CCAGCGTCGC TATCTTAGGG     180

GCTGGTTTTG TTGCGTCTCA GCCTACTGTT GTAAGAGCAG AAGAATCTCC CGTAGCCAGT     240
```

-continued

```
CAGTCTAAAG CTGAGAAAGA CTATGATGCA GCGAAGAAAG ATGCTAAGAA TGCGAAAAAA      300

GCAGTAGAAG ATGCTCAAAA GGCTTTAGAT GATGCAAAAG CTGCTCAGAA AAAATATGAC      360

GAGGATCAGA AGAAAACTGA GGAGAAAGCC GCGCTAGAAA AAGCAGCGTC TGAAGAGATG      420

GATAAGGCAG TGGCAGCAGT TCAACAAGCG TATCTAGCCT ATCAACAAGC TACAGACAAA      480

GCCGCAAAAG ACGCAGCAGA TAAGATGATA GATGAAGCTA AGAAACGCGA AGAAGAGGCA      540

AAAACTAAAT TTAATACTGT TCGAGCAATG GTAGTTCCTG AGCCAGAGCA GTTGGCTGAG      600

ACTAAGAAAA AATCAGAAGA AGCTAAACAA AAAGCACCAG AACTTACTAA AAACTAGAA       660

GAAGCTAAAG CAAAATTAGA AGAGGCTGAG AAAAAAGCTA CTGAAGCCAA ACAAAAAGTG      720

GATGCTGAAG AAGTCGCTCC TCAAGCTAAA ATCGCTGAAT TGGAAAATCA AGTTCATAGA      780

CTAGAACAAG AGCTCAAAGA GATTGATGAG TCTGAATCAG AAGATTATGC TAAAGAAGGT      840

TTCCGTGCTC CTCTTCAATC TAAATTGGAT GCCAAAAAAG CTAAACTATC AAAACTTGAA      900

GAGTTAAGTG ATAAGATTGA TGAGTTAGAC GCTGAAATTG CAAAACTTGA AGATCAACTT      960

AAAGCTGCTG AAGAAAACAA TAATGTAGAA GACTACTTTA AGAAGGTTT AGAGAAAACT     1020

ATTGCTGCTA AAAAGCTGA ATTAGAAAAA ACTGAAGCTG ACCTTAAGAA AGCAGTTAAT     1080

GAGCCAGAAA AACCAGCTCC AGCTCCAGAA ACTCCAGCCC CAGAAGCACC AGCTGAACAA     1140

CCAAAACCAG CGCCGGCTCC TCAACCAGCT CCCGCACCAA AACCAGAGAA GCCAGCTGAA     1200

CAACCAAAAC CAGAAAAAAC AGATGATCAA CAAGCTGAAG AAGACTATGC TCGTAGATCA     1260

GAAGAAGAAT ATAATCGCTT GACTCAACAG CAACCGCCAA AAGCTGAAAA ACCAGCTCCT     1320

GCACCAAAAA CAGGCTGGAA ACAAGAAAAC GGTATGTGGT ACTTCTACAA TACTGATGGT     1380

TCAATGGCGA CAGGATGGCT CCAAAACAAC GGTTCATGGT ACTACCTCAA CAGCAATGGT     1440

GCTATGGCTA CAGGTTGGCT CCAATACAAT GGTTCATGGT ATTACCTCAA CGCTAACGGC     1500

GCTATGGCAA CAGGTTGGGC TAAAGTCAAC GGTTCATGGT ACTACCTCAA CGCTAATGGT     1560

GCTATGGCTA CAGGTTGGCT CCAATACAAT GGTTCATGGT ATTACCTCAA CGCTAACGGC     1620

GCTATGGCAA CAGGTTGGGC TAAAGTCAAC GGTTCATGGT ACTACCTCAA CGCTAATGGT     1680

GCTATGGCTA CAGGTTGGCT CCAATACAAC GGTTCATGGT ACTACCTCAA CGCTAACGGT     1740

GCTATGGCTA CAGGTTGGGC TAAAGTCAAC GGTTCATGGT ACTACCTCAA CGCTAATGGT     1800

GCTATGGCAA CAGGTTGGGT GAAAGATGGA GATACCTGGT ACTATCTTGA AGCATCAGGT     1860

GCTATGAAAG CAAGCCAATG GTTCAAAGTA TCAGATAAAT GGTACTATGT CAATGGTTTA     1920

GGTGCCCTTG CAGTCAACAC AACTGTAGAT GGCTATAAAG TCAATGCCAA TGGTGAATGG     1980

GTTTAAGCCG ATTAAATTAA AGCATGTTAA GAACATTTGA CATTTAATT TTGAAACAAA      2040

GATAAGGTTC GATTGAATAG ATTTATGTTC GTATTCTTTA GGTACC                   2086
```

(2) INFORMATION FOR SEQ ID NO:2:

(i) SEQUENCE CHARACTERISTICS:
        (A) LENGTH: 619 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met Asn Lys Lys Met Ile Leu Thr Ser Leu Ala Ser Val Ala Ile
1               5                   10                  15

Leu Gly Ala Gly Phe Val Ala Ser Gln Pro Thr Val Val Arg Ala Glu
```

-continued

```
                20                  25                  30
Glu Ser Pro Val Ala Ser Gln Ser Lys Ala Glu Lys Asp Tyr Asp Ala
         35                  40                  45
Ala Lys Lys Asp Ala Lys Asn Ala Lys Lys Ala Val Glu Asp Ala Gln
 50                  55                  60
Lys Ala Leu Asp Asp Ala Lys Ala Gln Lys Lys Tyr Asp Glu Asp
 65                  70                  75                  80
Gln Lys Lys Thr Glu Glu Lys Ala Ala Leu Glu Lys Ala Ala Ser Glu
                 85                  90                  95
Glu Met Asp Lys Ala Val Ala Ala Val Gln Gln Ala Tyr Leu Ala Tyr
             100                 105                 110
Gln Gln Ala Thr Asp Lys Ala Lys Asp Ala Asp Lys Met Ile
             115                 120                 125
Asp Glu Ala Lys Lys Arg Glu Glu Ala Lys Thr Lys Phe Asn Thr
         130                 135                 140
Val Arg Ala Met Val Val Pro Glu Pro Glu Gln Leu Ala Glu Thr Lys
145                 150                 155                 160
Lys Lys Ser Glu Glu Ala Lys Gln Lys Ala Pro Glu Leu Thr Lys Lys
                 165                 170                 175
Leu Glu Glu Ala Lys Ala Lys Leu Glu Glu Ala Glu Lys Lys Ala Thr
             180                 185                 190
Glu Ala Lys Gln Lys Val Asp Ala Glu Glu Val Ala Pro Gln Ala Lys
             195                 200                 205
Ile Ala Glu Leu Glu Asn Gln Val His Arg Leu Glu Gln Glu Leu Lys
         210                 215                 220
Glu Ile Asp Glu Ser Glu Ser Glu Asp Tyr Ala Lys Glu Gly Phe Arg
225                 230                 235                 240
Ala Pro Leu Gln Ser Lys Leu Asp Ala Lys Lys Ala Lys Leu Ser Lys
                 245                 250                 255
Leu Glu Glu Leu Ser Asp Lys Ile Asp Glu Leu Asp Ala Glu Ile Ala
             260                 265                 270
Lys Leu Glu Asp Gln Leu Lys Ala Ala Glu Glu Asn Asn Asn Val Glu
             275                 280                 285
Asp Tyr Phe Lys Glu Gly Leu Glu Lys Thr Ile Ala Ala Lys Lys Ala
         290                 295                 300
Glu Leu Glu Lys Thr Glu Ala Asp Leu Lys Lys Ala Val Asn Glu Pro
305                 310                 315                 320
Glu Lys Pro Ala Pro Ala Pro Glu Thr Pro Ala Pro Glu Ala Pro Ala
                 325                 330                 335
Glu Gln Pro Lys Pro Ala Pro Ala Pro Gln Pro Ala Pro Ala Pro Lys
             340                 345                 350
Pro Glu Lys Pro Ala Glu Gln Pro Lys Pro Glu Lys Thr Asp Asp Gln
         355                 360                 365
Gln Ala Glu Glu Asp Tyr Ala Arg Arg Ser Glu Glu Glu Tyr Asn Arg
         370                 375                 380
Leu Thr Gln Gln Pro Pro Lys Ala Glu Lys Pro Ala Pro Ala Pro
385                 390                 395                 400
Lys Thr Gly Trp Lys Gln Glu Asn Gly Met Trp Tyr Phe Tyr Asn Thr
                 405                 410                 415
Asp Gly Ser Met Ala Thr Gly Trp Leu Gln Asn Asn Gly Ser Trp Tyr
             420                 425                 430
Tyr Leu Asn Ser Asn Gly Ala Met Ala Thr Gly Trp Leu Gln Tyr Asn
         435                 440                 445
```

```
Gly Ser Trp Tyr Tyr Leu Asn Ala Asn Gly Ala Met Ala Thr Gly Trp
    450                 455                 460
Ala Lys Val Asn Gly Ser Trp Tyr Tyr Leu Asn Ala Asn Gly Ala Met
465                 470                 475                 480
Ala Thr Gly Trp Leu Gln Tyr Asn Gly Ser Trp Tyr Tyr Leu Asn Ala
                485                 490                 495
Asn Gly Ala Met Ala Thr Gly Trp Ala Lys Val Asn Gly Ser Trp Tyr
            500                 505                 510
Tyr Leu Asn Ala Asn Gly Ala Met Ala Thr Gly Trp Leu Gln Tyr Asn
        515                 520                 525
Gly Ser Trp Tyr Tyr Leu Asn Ala Asn Gly Ala Met Ala Thr Gly Trp
    530                 535                 540
Ala Lys Val Asn Gly Ser Trp Tyr Tyr Leu Asn Ala Asn Gly Ala Met
545                 550                 555                 560
Ala Thr Gly Trp Val Lys Asp Gly Asp Thr Trp Tyr Tyr Leu Glu Ala
                565                 570                 575
Ser Gly Ala Met Lys Ala Ser Gln Trp Phe Lys Val Ser Asp Lys Trp
            580                 585                 590
Tyr Tyr Val Asn Gly Leu Gly Ala Leu Ala Val Asn Thr Thr Val Asp
        595                 600                 605
Gly Tyr Lys Val Asn Ala Asn Gly Glu Trp Val
    610                 615

(2) INFORMATION FOR SEQ ID NO:3:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Glu Glu Ser Pro Val Ala Ser Gln Ser Lys Ala Glu Lys Asp Tyr Asp
1               5                   10                  15
Ala Ala Lys Lys Asp Ala Lys Asn Ala Lys Lys Ala Val Glu Asp Ala
            20                  25                  30
Gln Lys Ala Leu Asp Asp Ala Lys Ala Ala Gln Lys Lys
        35                  40                  45

(2) INFORMATION FOR SEQ ID NO:4:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Glu Glu Ser Pro Val Ala Ser Gln Ser Lys Ala Glu Lys Asp Tyr Asp
1               5                   10                  15
Ala Ala Lys Lys Asp Ala Lys Asn Ala Lys Lys Ala Val Glu Asp Ala
            20                  25                  30
Gln Lys Ala Leu Asp Asp Ala Lys Ala Ala Gln Lys Lys Tyr Asp Glu
        35                  40                  45
Asp Gln Lys Lys Thr Glu Glu Lys Ala Ala Leu Glu Lys Ala Ala Ser
    50                  55                  60
```

```
Glu Glu Met Asp Lys Ala Val Ala Ala Val Gln Gln Ala Tyr Leu Ala
 65                  70                  75                  80

Tyr Gln Gln Ala Thr Asp Lys Ala Ala Lys Asp Ala Ala Asp Lys Met
                 85                  90                  95

Ile Asp Glu Ala Lys Lys Arg Glu Glu Ala Lys Thr Lys Phe Asn
                100                 105                 110

Thr Val Arg Ala Met Val Val Pro Glu Pro Glu Gln Leu Ala Glu Thr
            115                 120                 125

Lys Lys Lys Ser Glu Glu Ala Lys Gln Lys Ala Pro Glu Leu Thr Lys
130                 135                 140

Lys Leu Glu Glu Ala Lys Ala Lys Leu Glu Glu Ala Glu Lys Lys Ala
145                 150                 155                 160

Thr Glu Ala Lys Gln Lys Val Asp Ala Glu Val Ala Pro Gln Ala
                165                 170                 175

Lys Ile Ala Glu Leu Glu Asn Gln Val His Arg Leu Glu Gln Glu Leu
                180                 185                 190

Lys Glu Ile Asp Glu Ser Glu Ser Glu Asp Tyr Ala Lys Glu Gly Phe
                195                 200                 205

Arg Ala Pro Leu Gln Ser Lys Leu Asp Ala Lys Lys Ala Lys Leu Ser
            210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
                245                 250                 255

Glu Asp Tyr Phe Lys Glu Gly Leu Glu Lys Thr Ile Ala Ala Lys Lys
                260                 265                 270

Ala Glu Leu Glu Lys Thr Glu Ala Asp Leu Lys Lys Ala Val Asn Glu
            275                 280                 285

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CCGGATCCAG CTCCTGCACC AAAAAC                                       26

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGCGTCGAC GGCTTAAACC CATTCACCAT TGG                               33
```